US012664914B2

(12) United States Patent

Fernandez et al.

(10) Patent No.: US 12,664,914 B2

(45) Date of Patent: *Jun. 23, 2026

(54) TOTAL MESORECTAL EXCISION SURGICAL SIMULATOR

(71) Applicant: Applied Medical Resources Corporation, Rancho Santa Margarita, CA (US)

(72) Inventors: Anysa Fernandez, Chino, CA (US); Gregory Hofstetter, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/495,576

(22) Filed: Oct. 26, 2023

(65) Prior Publication Data

US 2024/0054917 A1 Feb. 15, 2024

Related U.S. Application Data

(63) Continuation of application No. 17/717,443, filed on Apr. 11, 2022, now Pat. No. 11,837,109, which is a (Continued)

(51) Int. Cl.
G09B 23/34 (2006.01)
A61B 17/00 (2006.01)
(Continued)

(52) U.S. Cl.
CPC ............. G09B 23/34 (2013.01); G09B 23/28 (2013.01); G09B 23/30 (2013.01); A61B 2017/00716 (2013.01)

(58) Field of Classification Search
CPC .... G09B 23/28; G09B 23/281; G09B 23/285; G09B 23/30; G09B 23/32; G09B 23/34; A61B 2017/00716

(Continued)

(56) References Cited

U.S. PATENT DOCUMENTS 5,425,644 A 6/1995 Szinicz
5,947,743 A * 9/1999 Hasson ................ G09B 23/286
434/262

(Continued)

FOREIGN PATENT DOCUMENTS

CN 2909427 Y 6/2007
WO WO 2012/149606 A1 11/2012

(Continued)

OTHER PUBLICATIONS

European Patent Office, The International Search Report and Written Opinion for International Application No. PCT/US2018/066574, entitled "Total Mesorectal Excision Surgical Simulator," mailed May 7, 2019, 25 pgs.

*Primary Examiner* — Joseph B Baldori

(74) *Attorney, Agent, or Firm* — Patrick Ikehara

(57) ABSTRACT

A TME surgical simulator is provided. The TME surgical simulator includes a simulated tissue layers and simulated vasculature and/or organ structures. The simulated tissue surgical simulator is adapted for but not limited to laparoscopic and/or transanal TME surgical procedures.

17 Claims, 26 Drawing Sheets

Related U.S. Application Data continuation of application No. 16/226,295, filed on Dec. 19, 2018, now Pat. No. 11,302,219.

(60) Provisional application No. 62/607,476, filed on Dec. 19, 2017.

(51) Int. Cl.
G09B 23/28 (2006.01)
G09B 23/30 (2006.01)

(58) Field of Classification Search
USPC ................................. 434/267, 269, 272, 273
See application file for complete search history.

(56) References Cited

U.S. PATENT DOCUMENTS

| | | | |
|---|---|---|---|
| 7,553,159 B1 | 6/2009 | Arnal et al. | |
| 7,665,995 B2 * | 2/2010 | Toly ..................... | G09B 23/285 434/262 |
| 7,857,626 B2 * | 12/2010 | Toly ........................ | G09B 23/28 434/262 |
| 7,931,471 B2 | 4/2011 | Senagore et al. | |
| 8,297,982 B2 * | 10/2012 | Park ........................ | G09B 23/34 434/262 |
| 8,556,635 B2 * | 10/2013 | Toly ..................... | G09B 23/285 434/262 |
| 9,123,261 B2 | 9/2015 | Lowe | |
| 9,805,624 B2 | 10/2017 | Reihsen et al. | |
| 11,302,219 B2 * | 4/2022 | Fernandez ............. | G09B 23/34 |
| 2005/0008997 A1 | 1/2005 | Herman | |
| 2008/0064017 A1 * | 3/2008 | Grundmeyer, III .... | G09B 23/28 434/262 |
| 2009/0246747 A1 | 10/2009 | Buckman, Jr. | |
| 2010/0196867 A1 * | 8/2010 | Geerligs ................. | G09B 23/28 434/272 |
| 2012/0015337 A1 | 1/2012 | Hendrickson et al. | |
| 2013/0137075 A1 | 5/2013 | Forsythe | |
| 2014/0087345 A1 | 3/2014 | Breslin et al. | |
| 2014/0087347 A1 * | 3/2014 | Tracy ................... | G09B 23/285 434/272 |
| 2014/0220532 A1 * | 8/2014 | Ghez ...................... | G09B 23/30 434/272 |
| 2014/0248596 A1 | 9/2014 | Hart et al. | |
| 2015/0187229 A1 * | 7/2015 | Wachli ................... | G09B 23/30 434/272 |
| 2015/0371560 A1 | 12/2015 | Lowe | |
| 2016/0027344 A1 | 1/2016 | Felsinger et al. | |
| 2016/0232819 A1 | 8/2016 | Hofstetter et al. | |
| 2016/0287339 A1 * | 10/2016 | Bin Abdul Rahman .................... | A61B 8/00 |
| 2016/0293055 A1 | 10/2016 | Hofstetter | |
| 2016/0355676 A1 | 12/2016 | Felsinger et al. | |
| 2016/0365007 A1 | 12/2016 | Black et al. | |
| 2017/0018206 A1 | 1/2017 | Hofstetter et al. | |
| 2017/0148356 A1 | 5/2017 | Black et al. | |
| 2017/0186340 A1 * | 6/2017 | Ogawa ..................... | B32B 5/32 |
| 2018/0075777 A1 * | 3/2018 | Iverson ................. | G09B 23/30 |
| 2019/0287425 A1 * | 9/2019 | Hofstetter .............. | G09B 23/34 |

FOREIGN PATENT DOCUMENTS

| | | |
|---|---|---|
| WO | WO 2017/059417 A1 | 4/2017 |
| WO | WO 2017/173520 A1 | 10/2017 |

* cited by examiner

41

42

TOTAL MESORECTAL EXCISION SURGICAL SIMULATOR

CROSS-REFERENCE TO RELATED APPLICATIONS

This application is a continuation of U.S. patent application Ser. No. 17/717,443, filed Apr. 11, 2022, which is a continuation of U.S. patent application Ser. No. 16/226,295, filed Dec. 19, 2018, now issued U.S. Pat. No. 11,302,219, which claims the benefit of U.S. Provisional patent application No. 62/607,476, filed on Dec. 19, 2017, the entire disclosure of which is hereby incorporated by reference as if set in full herein.

BACKGROUND

This application is generally related to surgical training systems and methods, and, in particular to, simulated tissue structures and models for teaching, practicing and evaluating various surgical techniques and procedures related to but not limited to total mesorectal excision procedures and techniques.

Medical students as well as experienced doctors learning new surgical techniques must undergo extensive training before, they are qualified to perform surgery on human patients. The training must teach proper techniques employing various medical devices for cutting, penetrating, clamping, grasping, stapling, cauterizing and suturing a variety of tissue types. The range of possibilities that a trainee may encounter is great. For example, different organs and patient anatomies and diseases are presented. The thickness and consistency of the various tissue layers will also vary from one part of the body to the next and from one patient to another. Different procedures demand different skills. Furthermore, the trainee must practice techniques in various anatomical environs that are influenced by factors such as the size and condition of the patient, the adjacent anatomical landscape and the types of targeted tissues and whether they are readily accessible or relatively inaccessible.

Various teaching aids, trainers, simulators and model organs are available for one or more aspects of surgical training. However, there is a need for models or simulated tissue elements that are likely to be encountered in and that can be used for practicing endoscopic and laparoscopic, minimally invasive, transluminal surgical procedures. In laparoscopic surgery, a trocar or cannula is inserted to access a body cavity and to create a channel for the insertion of a camera such as a laparoscope. The camera provides a live video feed capturing images that are then displayed to the surgeon on one or more monitors. At least one additional small incision is made through which another trocar/cannula is inserted to create a pathway through which surgical instruments can be passed for performing procedures observed on the monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars. Laparoscopic surgery offers several advantages when compared with an open procedure but requires an increased level of skill as the target tissue is not directly observed by the clinician. The target tissue is observed on monitors displaying a portion of the surgical site that is accessed through a small opening. Therefore, clinicians need to practice visually determining tissue planes, three-dimensional depth perception on a two-dimensional viewing screen, hand-to-hand transfer of instruments, suturing, precision cutting and tissue and instrument manipulation. Typically One procedure is a total mesorectal excision (TME) for the treatment of late stage colorectal cancer in which the entire mesorectal envelope and a portion of the rectum are removed. This procedure has shown reduced local recurrence rates and improved oncologic outcomes for patients. The TME procedure can be performed using a combination of minimally invasive techniques, including laparoscopic and transanal approaches. Currently, there is an unmet need of educational tools for surgeons to utilize while developing and practicing skills relevant to the TME procedure.

SUMMARY

In accordance with various embodiments of the present invention, a TME surgical simulator is provided. The surgical simulator comprises a frame having a proximal opening and a distal opening and a simulated tissue layer connected and covering the proximal opening. In various embodiments, the surgical simulator further comprises a simulated organ assembly extending through the distal opening.

In various embodiments, a surgical simulator comprises a frame having a proximal portion defining a simulated abdominal cavity and a distal portion defining a simulated pelvic cavity and a simulated parietal peritoneum layer connected to the proximal portion. In various embodiments, the surgical simulator further comprises a simulated aorta disposed within the simulated abdominal cavity and a simulated prostate disposed within the simulated pelvic cavity.

In various embodiments, a surgical simulator comprises a simulated parietal peritoneum layer and a simulated mesorectum and mesentery layer connected to the simulated parietal peritoneum layer and together forming a envelope there between. In various embodiments, the surgical simulator further comprises a simulated fatty fill disposed within the envelope.

In various embodiments, a surgical simulator comprises a frame having a proximal portion defining a simulated abdominal cavity and a distal portion defining a simulated pelvic cavity, a simulated endopelvic fascia layer disposed within the simulated pelvic cavity and a simulated pelvic floor layer attached to the simulated endopelvic fascia layer and the distal portion of the frame. In various embodiments, the surgical simulator further comprises a simulated mesorectum layer attached to the simulated endopelvic fascia layer, the simulated mesorectum layer and the simulated endopelvic fascia layer defining a simulated dissection plane therebetween.

In various embodiments, a surgical simulator comprises a frame having a proximal portion defining a simulated abdominal cavity and a distal portion defining a simulated pelvic cavity, a simulated visceral peritoneum layer disposed within the simulated abdominal cavity and a simulated peritoneum or parietal peritoneum attached to the simulated visceral peritoneum layer and the proximal portion of the frame. In various embodiments, the surgical simulator further comprises a simulated mesentery layer attached to the simulated Toldt's/endopelvic fascia layer, the simulated mesentery layer and the simulated Toldt's/endopelvic fascia layer defining a simulated dissection plane there between.

Many of the attendant features of the present invention will be more readily appreciated as the same becomes better understood by reference to the foregoing and following description and considered in connection with the accompanying drawings.

BRIEF DESCRIPTION OF THE DRAWINGS

The present inventions may be understood by reference to the following description, taken in connection with the accompanying drawings in which the reference numerals designate like parts throughout the figures thereof.

DETAILED DESCRIPTION

Figure 1:
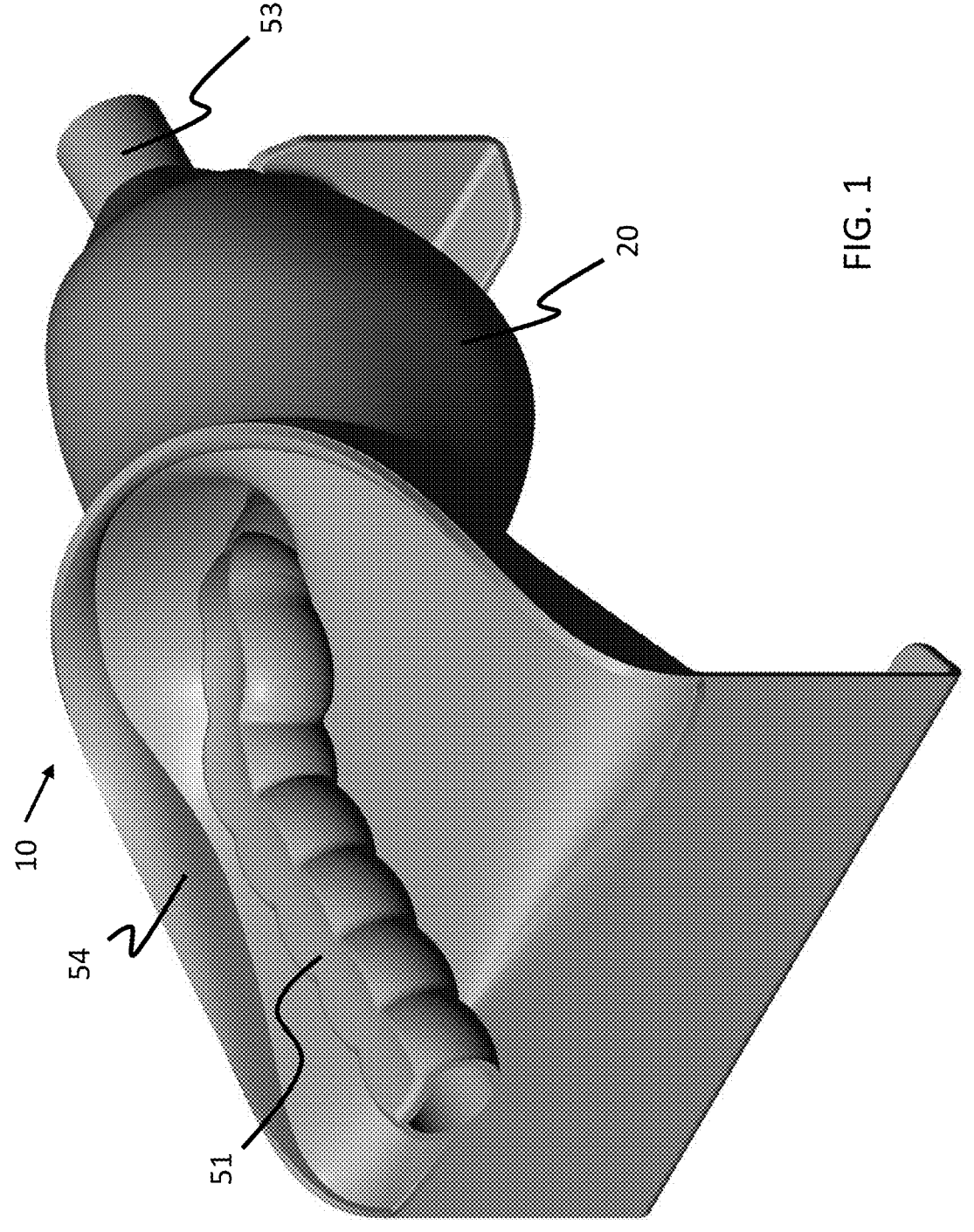
FIG. 1 is perspective view of a surgical simulator or model in accordance with various embodiments of the present invention.
Figure 2:
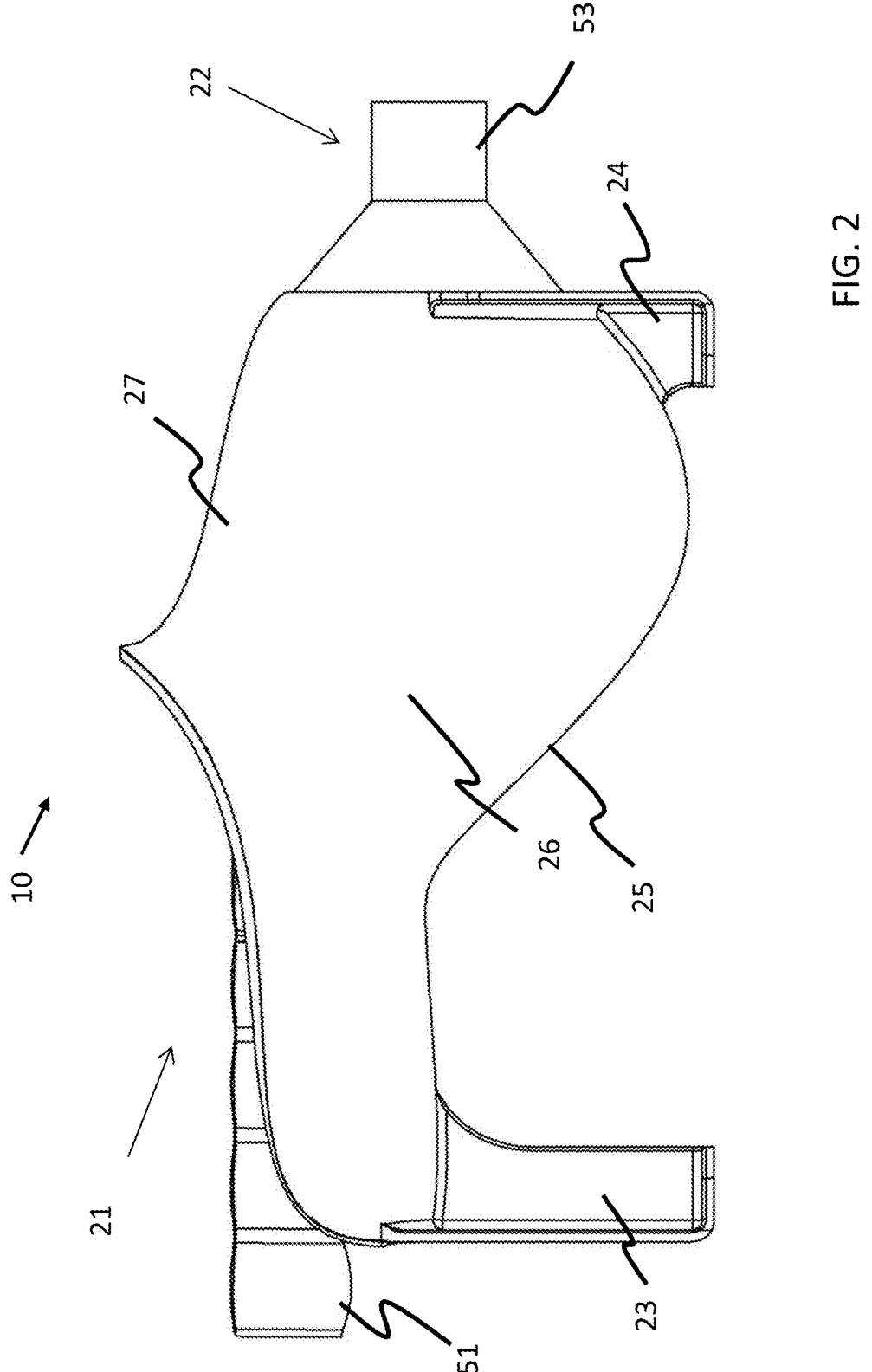
FIG. 2 is a side view of a surgical simulator in accordance with various embodiments of the present invention.
Figure 3:
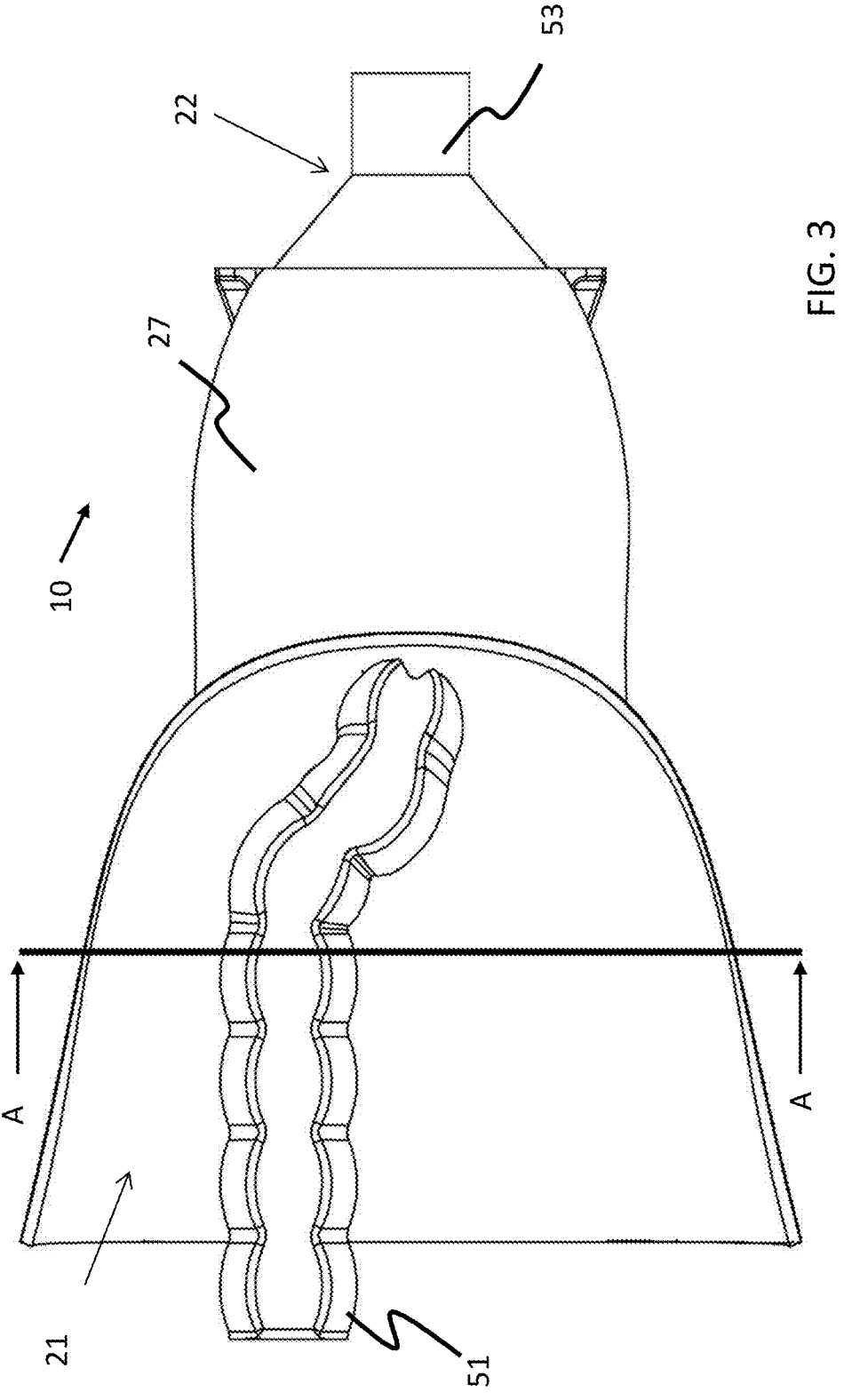
FIG. 3 is a top view of a surgical simulator in accordance with various embodiments of the present invention.
Figure 4A:
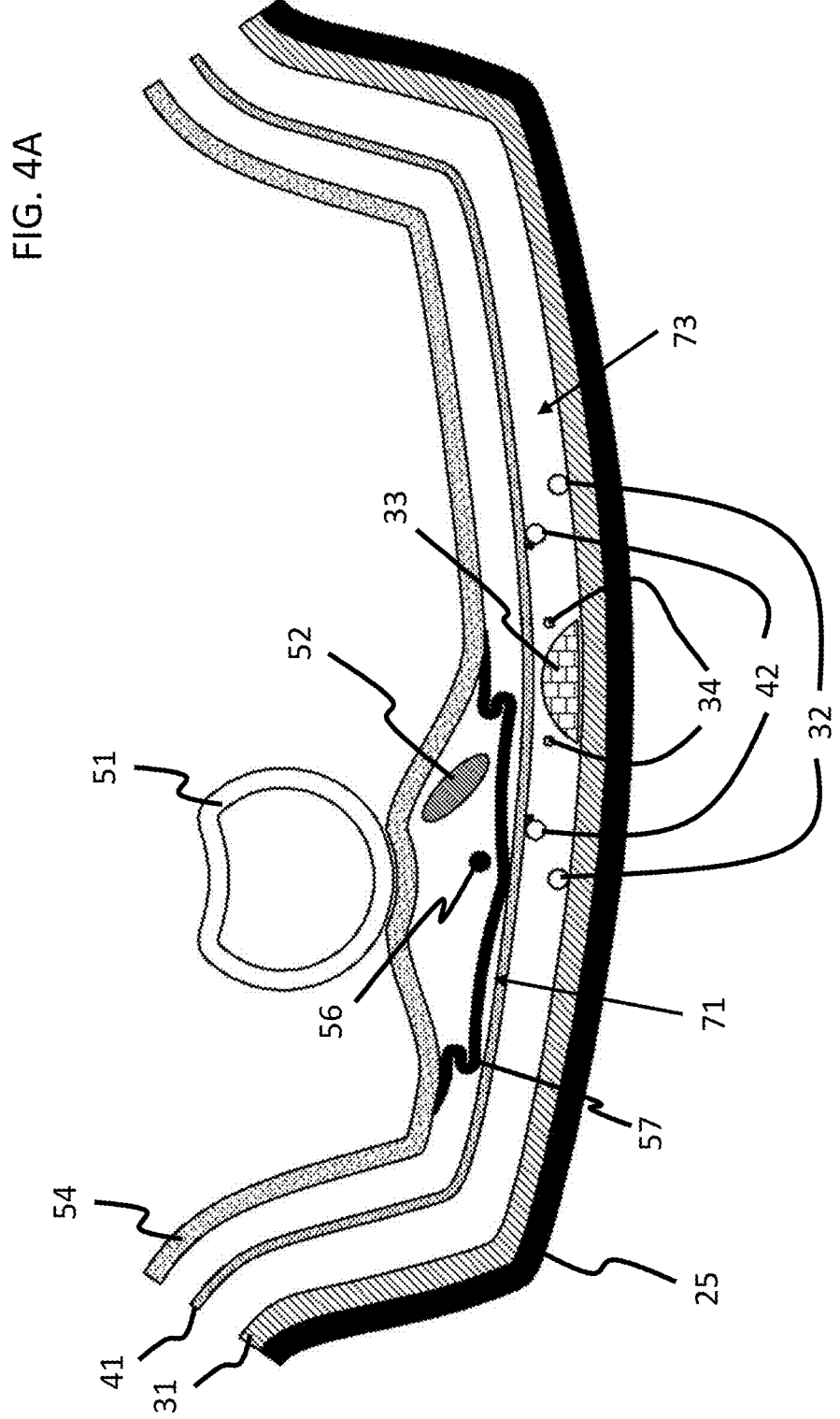
FIGS. 4A-4B are front cross-sectional semi-schematic diagrams of a surgical simulator in accordance with various embodiments of the present invention taken along the line A-A.
Figure 4B:
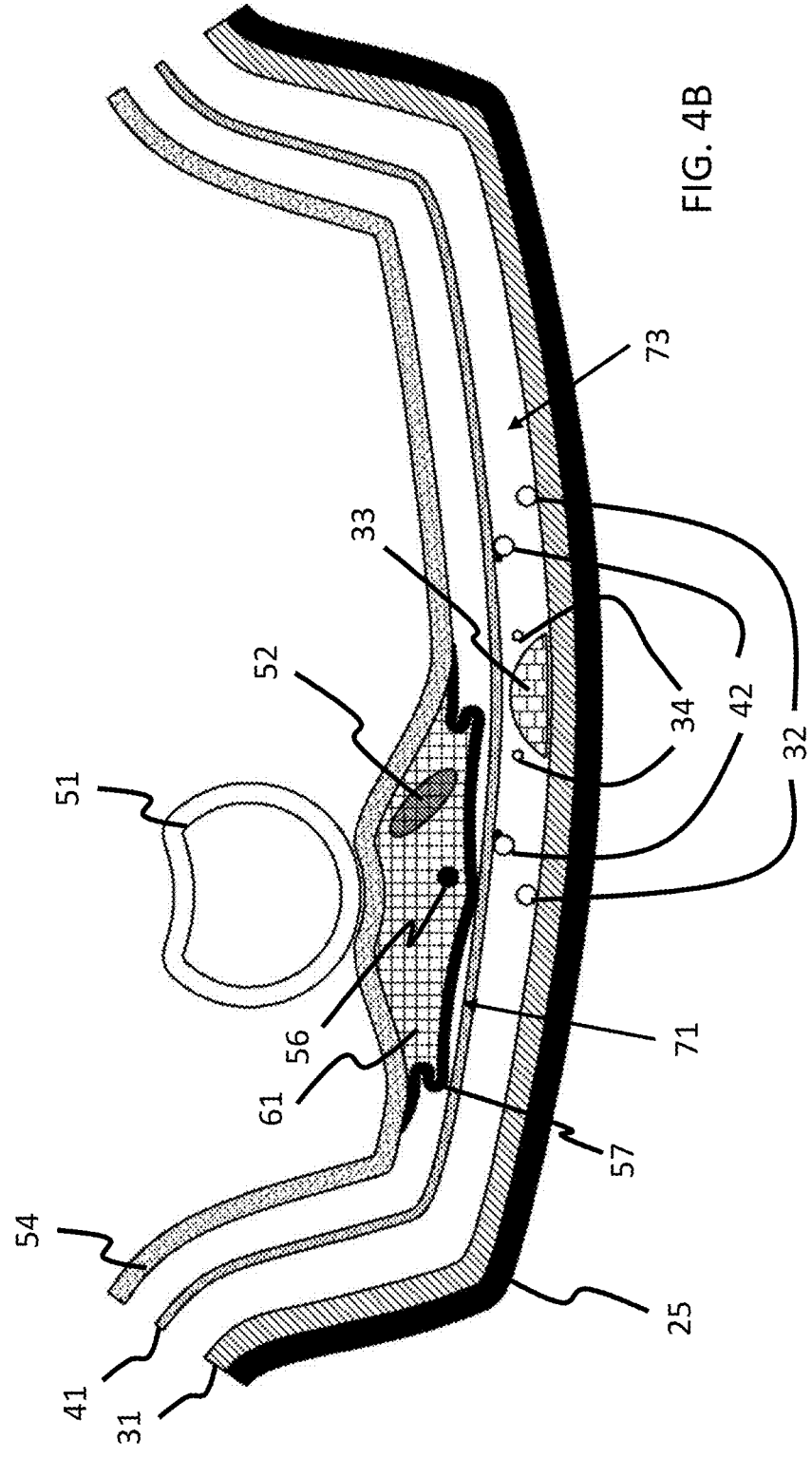
Figure 5A:
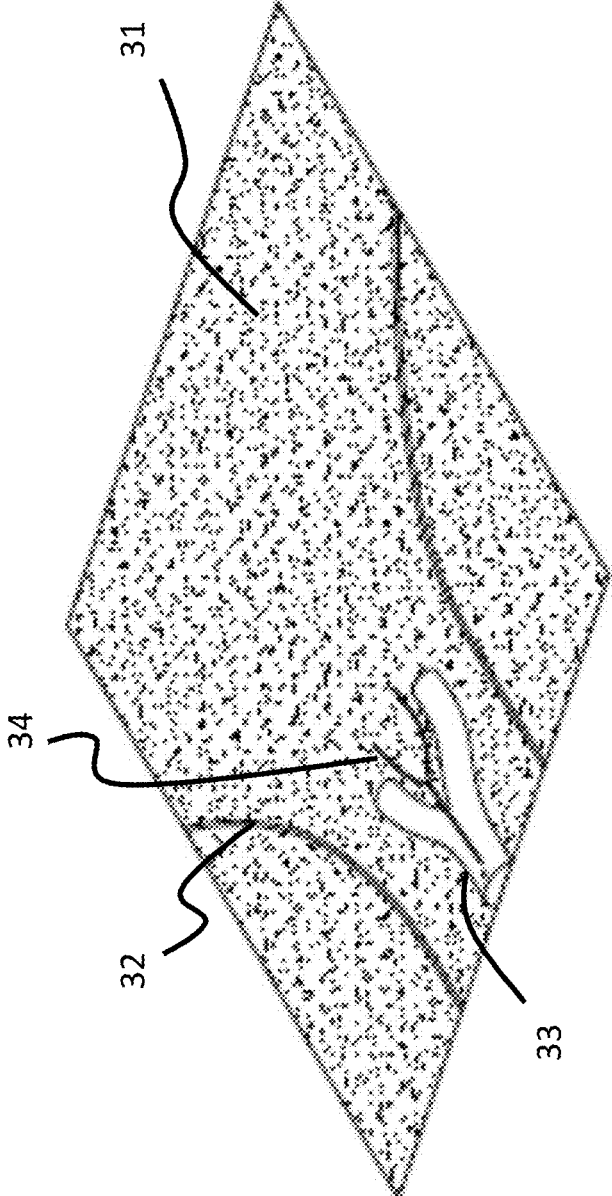
FIG. 5A is a perspective view of portions of a surgical simulator in accordance with various embodiments of the present invention.
Figure 5B:
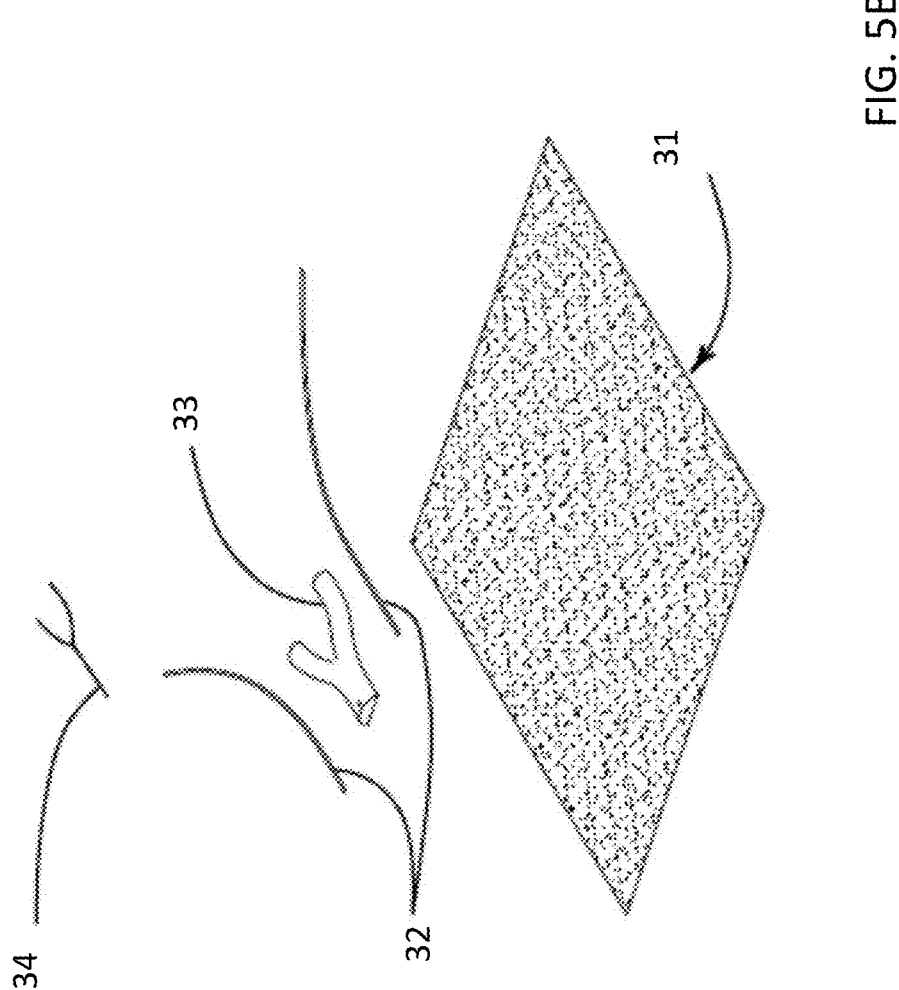
FIG. 5B is an exploded view of portions of a surgical simulator in accordance with various embodiments of the present invention.
Figure 6:
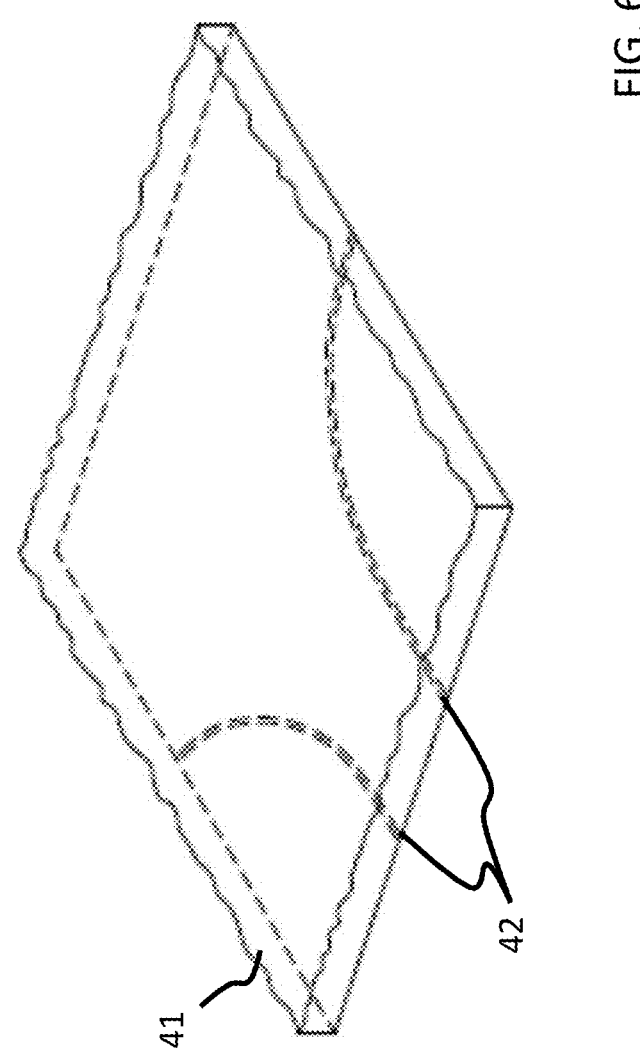
FIG. 6 is a perspective view of portions of a surgical simulator in accordance with various embodiments of the present invention.
Figure 7:
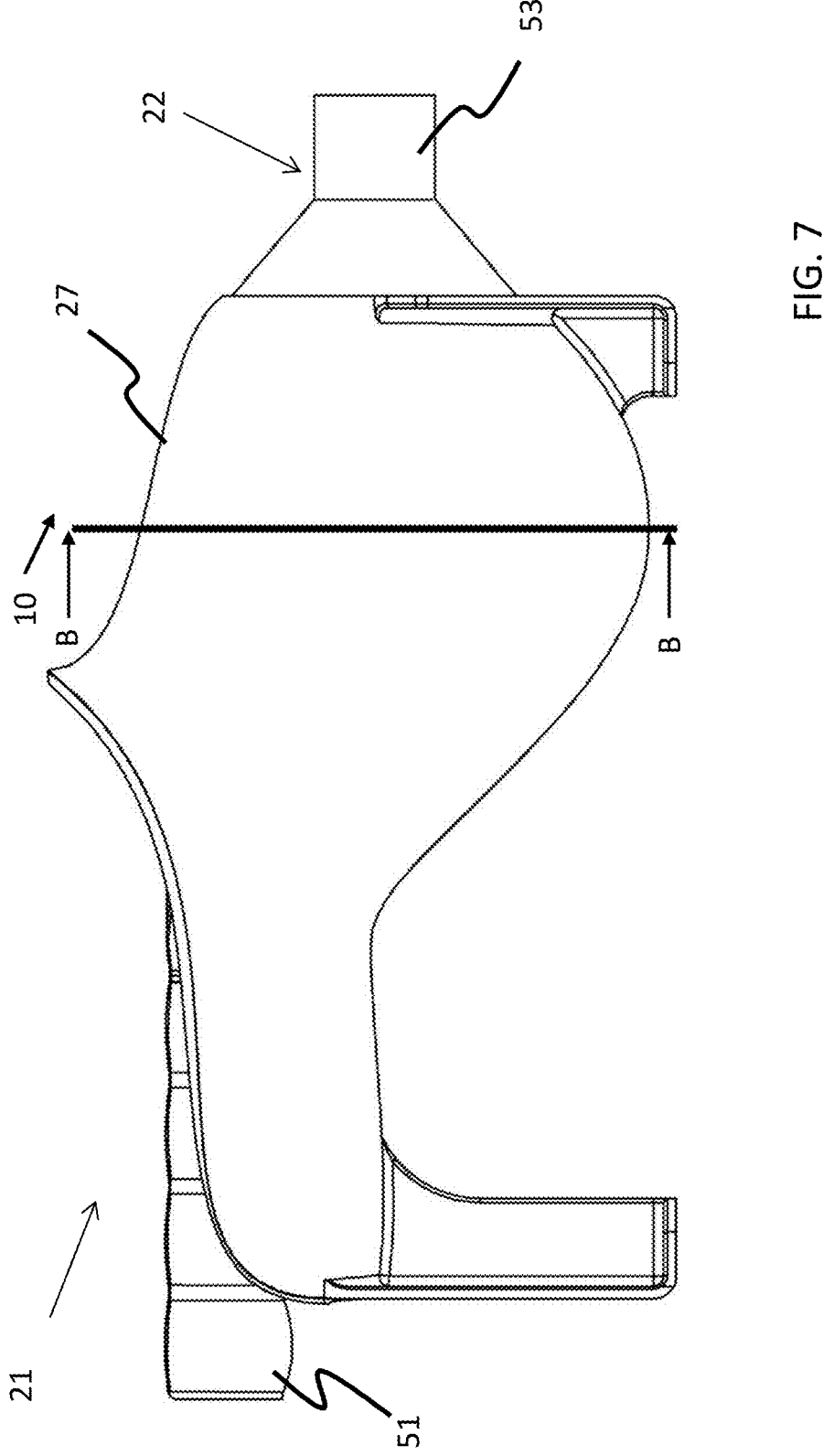
FIG. 7 is a side view of a surgical simulator in accordance with various embodiments of the present invention.
Figure 8A:
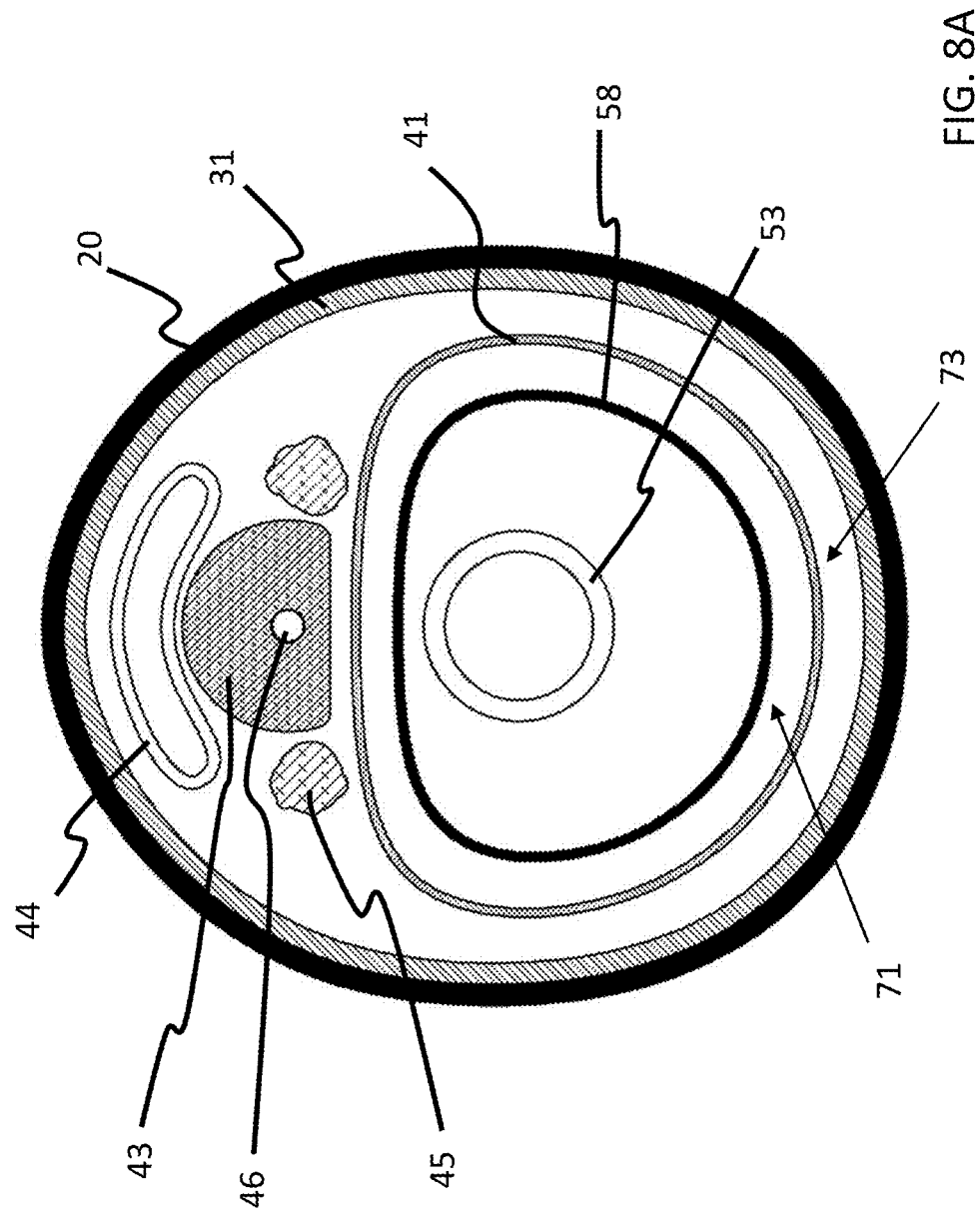
FIGS. 8A-8B are front cross-sectional semi-schematic diagrams of a surgical simulator in accordance with various embodiments of the present invention taken along the line B-B.
Figure 8B:
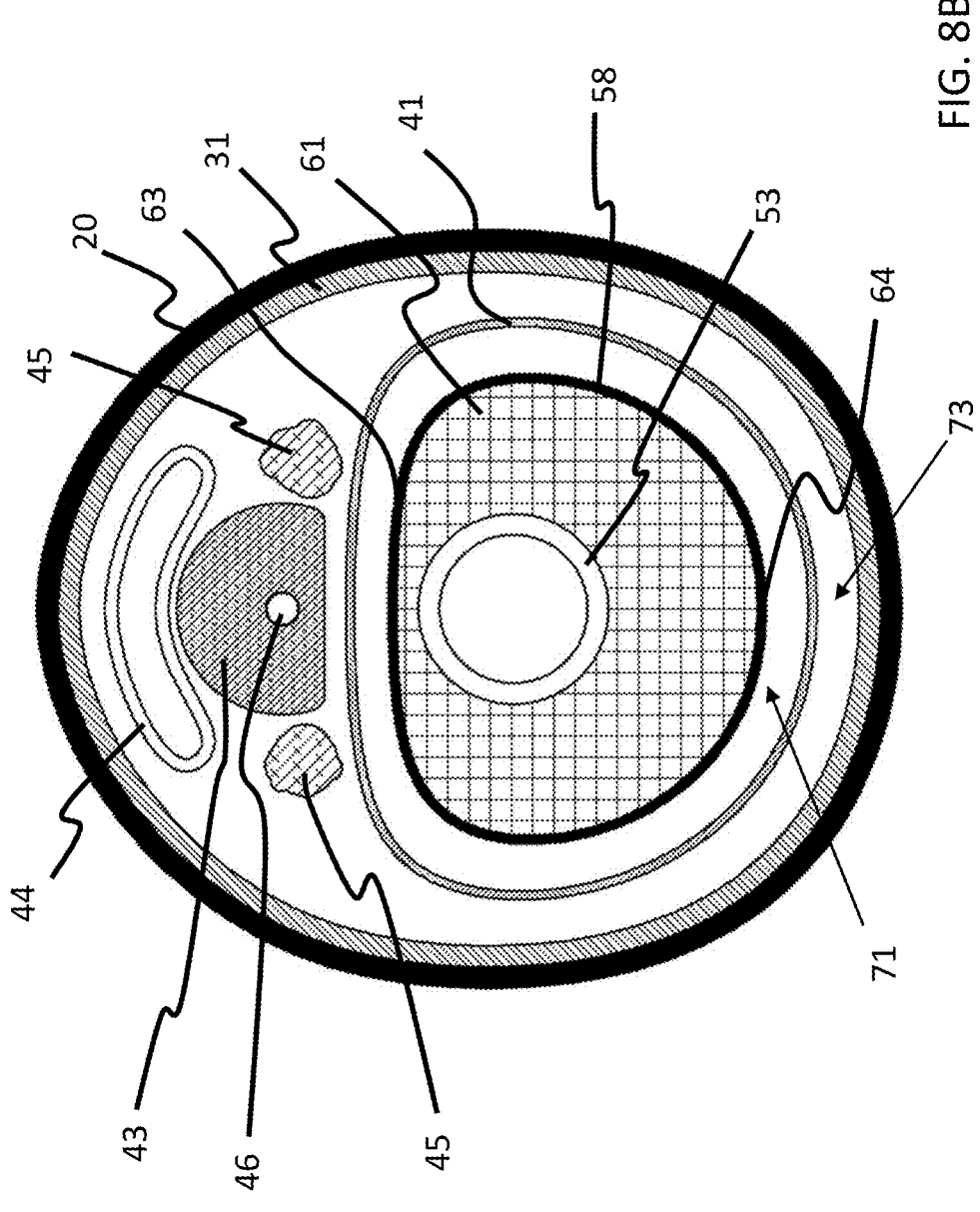
Figure 9:
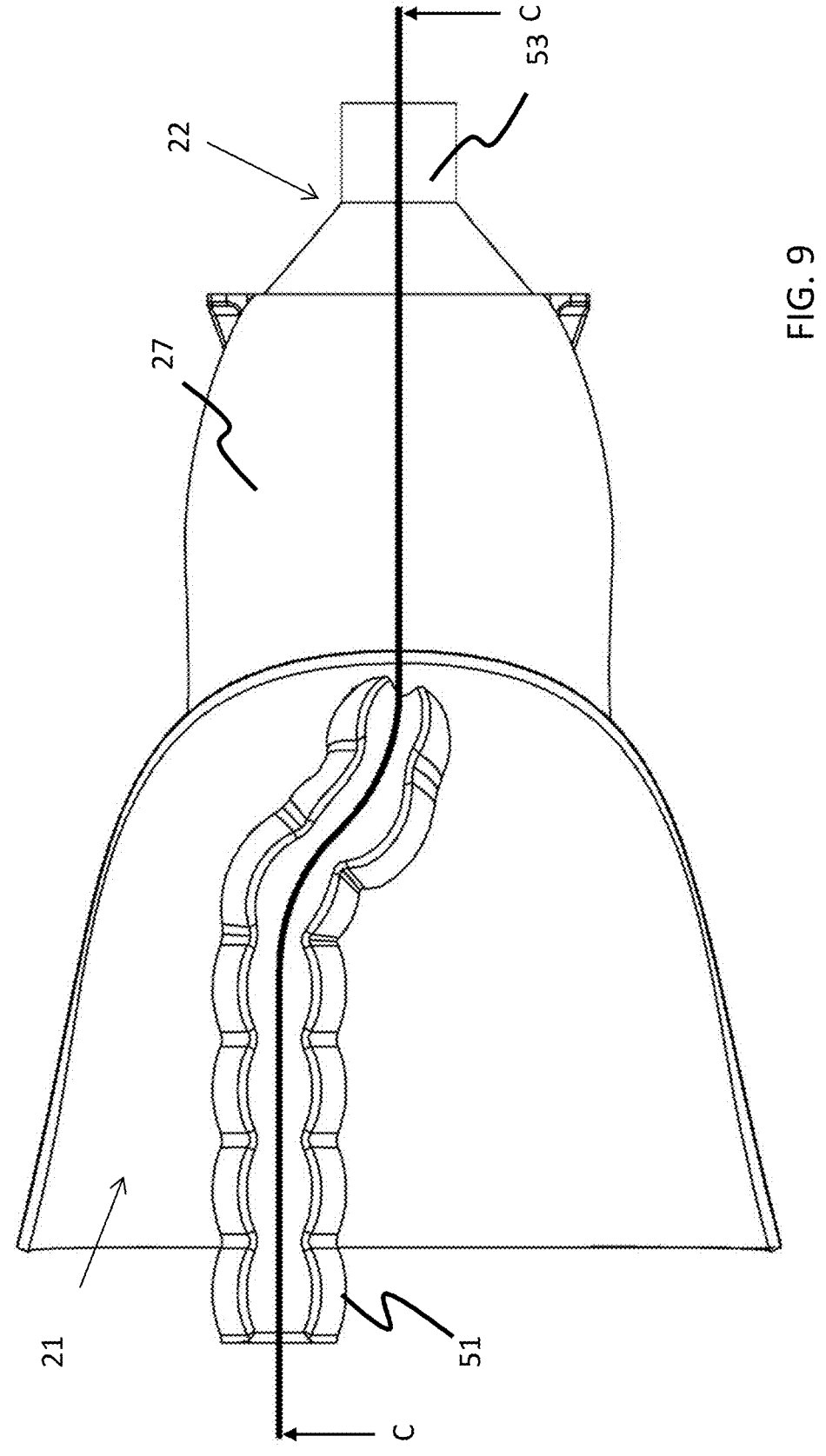
FIG. 9 is a top view of a surgical simulator in accordance with various embodiments of the present invention.
Figure 10A:
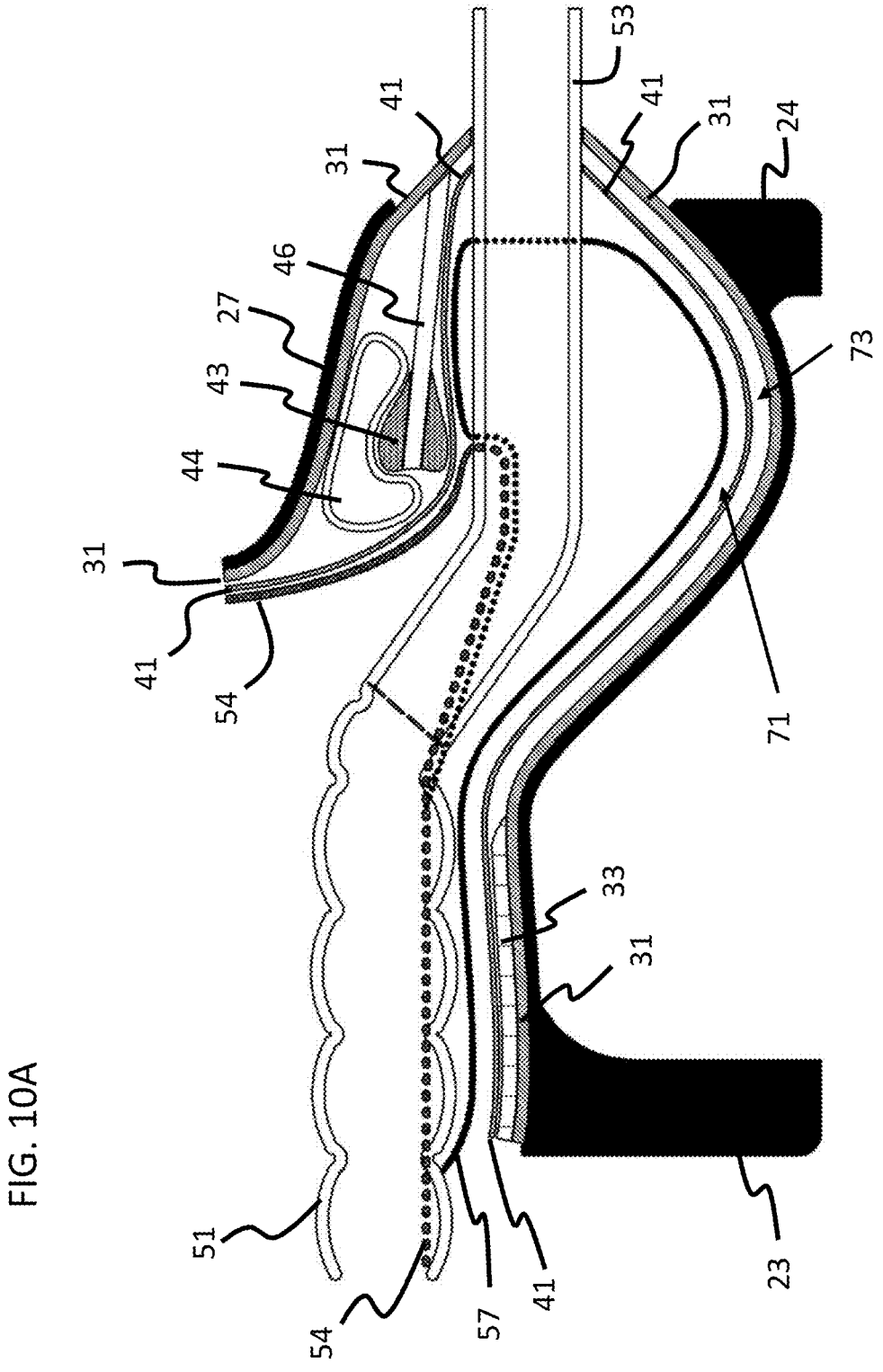
FIGS. 10A-10B are side cross-sectional semi-schematic diagrams of a surgical simulator in accordance with various embodiments of the present invention taken along the curved line C-C.
Figure 10B:
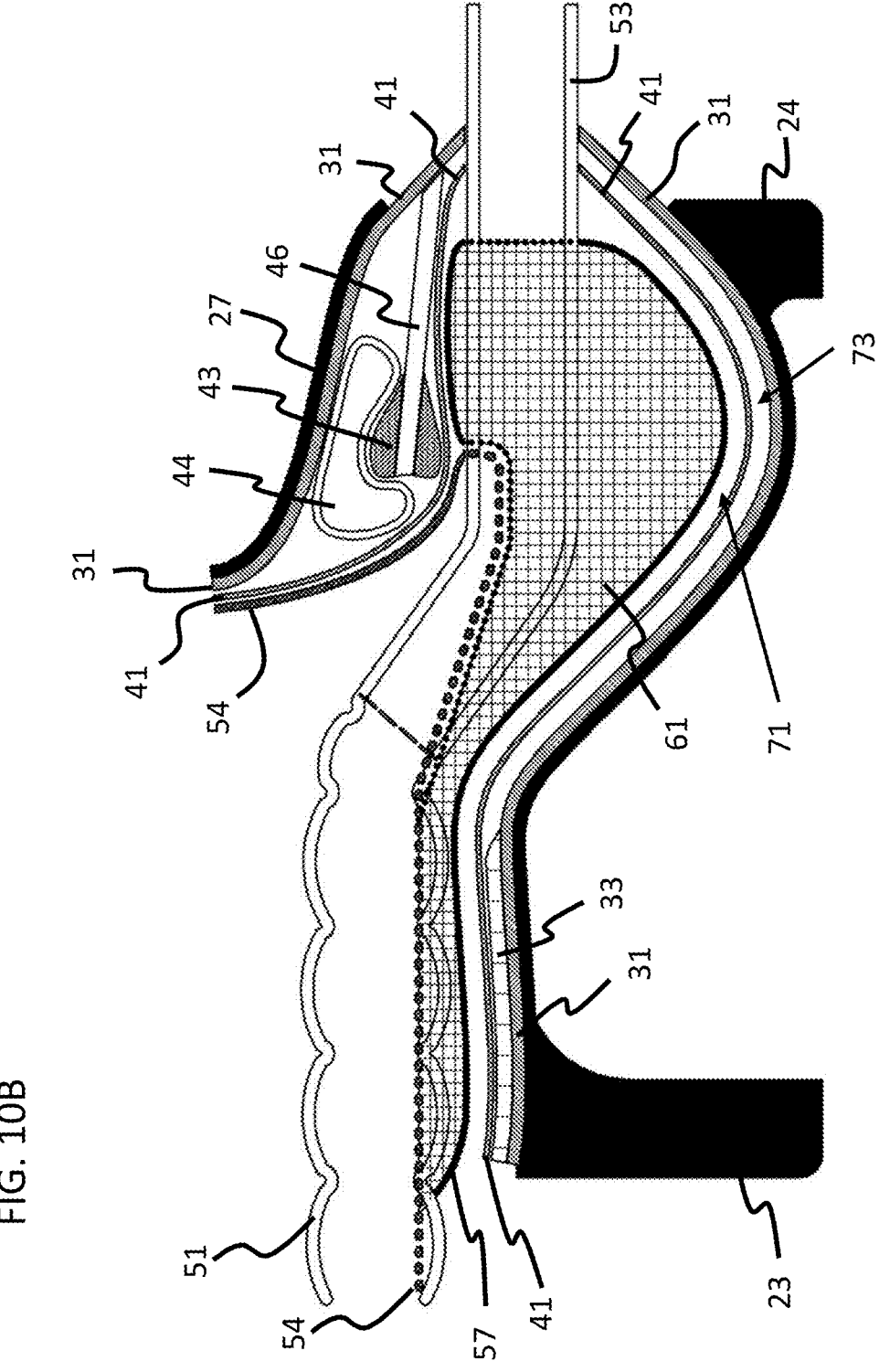

Generally, a TME surgical simulator or model is provided to assist in surgical skill training and simulation. The TME simulator comprises various simulated organ and/or tissue structure assemblies attached to each other and positioned within a rigid frame. The simulated organ structure assemblies provide different simulated tissue planes and in particular, distinguishable simulated dissection planes. Various features of the assemblies further provide added tactile and/or visual feedback along with difficulties and challenges to simulate and further assist in training and assessment of a simulated TME surgical procedure. For example, varying sizes and/or attachment of various simulated organ structures and/or varying various compositions and/or toughness of such structures and assemblies are provided.

During a TME procedure, the fatty mesorectal envelope circumferencing the rectum is removed along with a portion of the rectum. This procedure requires ligation of the relevant blood supply as well as circumferential mobilization of the rectum and mesorectum from the pelvic cavity and surrounding structures. Once the mesorectal specimen is removed, the mesorectum is inspected and graded; ranging from incomplete to complete dissection of this tissue. This is determined by visibility of the rectal lumen where segments of the mesorectum have been dissected into erroneously. Grading of the excised specimen can be used to assess surgical performance as well as local recurrence risk.

A TME procedure, as such, requires a high level of technical skill and understanding of the pelvic anatomy. The TME surgical simulator in various embodiments mimics a portion of the pelvic anatomy and thus can meet the clinical need in providing learning tools for surgeons to use during their education. The TME surgical simulator in accordance with various embodiments allows for the execution and/or completion of a simulated TME procedure from a laparoscopic and/or transanal approach. In accordance with various embodiments, for compatibility with both approaches and realistic identification of the relevant anatomical landmarks, the TME surgical simulator comprises at least one or more of the following simulated organ structures, tissue, vasculature and/or materials: colon, mesentery, mesorectum, Toldt's fascia, visceral peritoneum (retroperitoneum), endopelvic fascia, prostate, ureter, gonadal vessels, seminal vesicles, muscle layers, pelvic floor, IMA, IMV and aorta. The simulated materials, tissue layers and/or organ structures, in various embodiments, are also assembled in such a way that allows the end user, e.g., the surgeon, to perform the simulated procedure such that it provides realistic tactile feedback similar to that which one would encounter during the non-simulated procedure. This, among other things, allows the user to train on technical skill development associated with the identification of relevant anatomy and tissue handling. In accordance with various embodiments, the simulated materials can be confined within a simulated pelvis, which provides realistic limitations of the pelvic workspace including, for example, limited visualization occurring during dissection down the curved pelvic floor during a TME procedure. The simulated materials in various embodiments allows for the removal of the simulated mesorectum specimen which upon removal can be graded, for example, on a scale of 1-3 ranging from incomplete to complete dissection.

The TME surgical simulator according to various embodiments of the present invention is used to simulate a total mesorectal excision procedure. To provide a realistic procedural training environment, the TME surgical simulator or model provides laparoscopic and transanal access for the surgical procedure simulation. The surgical simulator provides simulated materials to represent the various anatomical landmarks and planes, as well as materials to simulate dissection, which provides notable visual and tactile feedback useful to understand the anatomy and tissue handling in order to better understand the complications that can be encountered during a surgical procedure. Additionally, the TME surgical simulator provides materials to simulate the mesorectum that allow the mesorectum to be mobilized, removed, and graded. Portions of the simulator, such as the mesorectum, are provided such that it is sufficiently fragile and thus able to be damaged during the simulated procedure. This in turn allows the simulated mesorectum and the like to be assessed and/or graded similar to a surgical procedure. In various embodiments, the confinement of portions of the surgical simulator in a simulated pelvis presents the realistic challenge of working within a confined space. Additionally, in various embodiments, the simulated pelvis has a curve integrated within its shape to simulate the curve of the sacrum, which presents a visualization challenge during the surgical procedure. The TME surgical simulator in various embodiments can be used within a laparoscopic trainer and with laparoscopic instruments for a simulated procedure. The TME surgical simulator, in accordance with various embodiments, relevant and realistic anatomy for the performance of each surgical step of the TME procedure.

Referring to FIGS. 1-3 and 14-20, the TME surgical simulator 10 comprises a simulated pelvic frame or base 20. The frame 20 in various embodiments is the hardest or most rigid portion of the simulator 10. The frame provides a platform raising and/or suspending simulated organ or tissue structures 100 secured to the frame. The frame has a proximal end and a distal end in which the proximal end has enlarged opening 21 relative to a restricted opening 22 at its distal end. In various embodiments, the frame is sized and shaped to fit within the confines of a laparoscopic trainer having specific and limited access points or channels to access the TME surgical simulator and/or not air tight or able to seal in insufflation gas.

A proximal portion of the simulator 10 is a simulated abdominal cavity or portions thereof and a distal portion of the simulator is a simulated pelvic cavity or portions thereof. As such, the proximal portion of the frame is set higher or above the distal portion of the frame. Similarly, simulated organ and/or tissue structures in the proximal portion are different from those in the distal portion of the simulator 10. However, some common organ and/or tissue structures extend from the proximal portion to the distal portion. In the illustrated embodiment, at or near the proximal end of the frame extends a support or leg 23 and at or near the distal end of the frame extends a support or leg 24. The leg 23 extends from a proximal portion of frame floor 25 and leg 24 extend from a distal portion of the frame floor 25 with the proximal portion of the frame floor being higher or positioned above the distal portion of the frame floor. The frame floor 25 extends into sidewalls 26 and at a distal portion extends to a roof or top 27. As such, in various embodiments, the distal portion of the frame provides a confined curved cavity or enclosure and at a distal end provides a generally circular opening and the proximal portion of the frame provides an enlarged curved cavity with an enlarged opening. The frame floor 25 in various embodiments starting at the proximal end of the frame extends laterally, curves down and back up at the distal end of the frame. In the illustrated embodiment, the legs and frame floor are integrated or formed as a single monolithic structure and in various embodiments are separate components, connected together to form a simulated working space for the simulator 10. In various embodiments, the frame is formed plastic or a similar rigid material and in other various embodiments includes plastic sheets cut to shape and attached together, e.g., with mechanical fasteners, to form the frame. Various simulated organ and tissue structures, assemblies or subassemblies are secured and/or supported by the frame.

Referring now also to FIGS. 4A-10B, the simulator 10 comprises a simulated pelvic floor assembly, a simulated Toldt's/endopelvic fascia assembly, a colon/rectum assembly and a mesentery/mesorectum assembly. The simulated pelvic floor assembly comprises simulated Gonadal vessels 32, simulated aorta 33 and simulated nerves 34 with a layer of fibrous material, such as batting, attaching or otherwise placing the simulated material between or intermingling with the fibrous material and a simulated pelvic floor 31. In various embodiments, simulated pelvic floor 31, simulated Gonadal vessels 32, simulated aorta 33 and simulated nerves 34 are all made of silicone but are colored or otherwise distinguished from each other visually and/or tactilely. Similarly, the simulated vessel structures have a different thickness or length to further distinguish the structures, such as the simulated aorta 33 being thicker than the simulated nerves 34 and the simulated gonadal vessels 32 and/or the simulated gonadal vessels being longer than the simulated nerves 34.

In accordance with various embodiments, the simulated Toldt's or endopelvic fascia assembly comprises a simulated Toldt's fascia/visceral peritoneum/endopelvic fascia sheet or layer 41 ("Toldt's/endopelvic fascia") and simulated ureters 42 and in various embodiments simulated blood vessels attached to the simulated ureters. The simulated Toldt's/ endopelvic fascia sheet in various embodiments is made from silicone and fibrous material, e.g., batting, attached or cured thereto. The simulated ureters and associated vessels are also made of silicone and are attached to the simulated Toldt's/endopelvic fascia sheet and in various embodiments adhered or attached to a proximal portion of the sheet and/or on a smooth or non-fibrous side of the sheet. In various embodiments, simulated ureters, vessels and Toldt's/endopelvic fascia sheet are colored or otherwise distinguished from each other visually, e.g., colored, and/or tactilely, e.g., having different dimensions, thickness and/or length.

In the illustrated embodiment, the simulated Gonadal vessels 32, simulated aorta 33 and simulated nerves 34 are adhered to the simulated pelvic floor 31 which is attached to the frame and a distal portion of the simulated pelvic floor away from the simulated aorta 33 is cut, folded and shaped also attached to the frame. The simulated Gonadal vessels 32, simulated aorta 33 and/or simulated nerves 34 are also only accessible and/or visible at or near the proximal portion of the TME surgical simulator while the simulated pelvic floor extends along or throughout the entire length or interior of the frame. The simulated ureters 42 are also only accessible and/or visible at or near the proximal portion of the TME surgical simulator and thereby further mimicking or closely representing portions of abdominal cavity in the TME surgical simulator. The Toldt's/endopelvic fascia sheet is adhered or otherwise attached to the pelvic floor placing the simulated ureters and vessel there between. Furthermore, a distal portion of the Toldt's/endopelvic fascia sheet is shaped, formed and/or attached to itself to provide a generally enclosed or circular or oval enclosure at the distal portion of the TME surgical simulator and thereby also further mimicking or more closely representing portions of the pelvic cavity in the TME surgical simulator.

In accordance with various embodiments, at a distal portion of the TME surgical simulator, a simulated prostate 43, simulated bladder 44 and simulated seminal vesicles 45 are also provided and attached to the simulated endopelvic sheet 41. As provided in the illustrated embodiment, the simulated bladder 44 is positioned above and somewhat around the simulated prostate 43 with the simulated prostate 43 having a simulated urethra 46 extending therefrom. The simulated seminal vesicles 45 are positioned adjacent or next to the simulated prostate 43 and in various embodiments, the simulated prostate 43, simulated bladder 44, simulated seminal vesicles 45 and/or simulated urethra 46 are disposed between the simulated pelvic floor 31 and the simulated endopelvic fascia sheet 41. In various embodiments, although not illustrated, the ureters attach to the bladder towards the proximal end of the surgical simulator. In various embodiments, the simulated pelvic floor 31 covers the simulated endopelvic fascia sheet 41 to form or define a cavity in which the simulated prostate 43, simulated bladder 44, simulated seminal vesicles 45 and/or simulated urethra 46 are captured or enclosed therein. In accordance with various embodiments, the simulated endopelvic fascia sheet 41 is adhered to the simulated pelvic floor 31, which is then placed under an outward tension or away from the interior of the frame but still within the confines of frame. In various embodiments, the simulated pelvic floor is stretched or pulled towards the interior of frame after being adhered to the frame to ultimately provide or assist in providing the outward tension for the simulated pelvic floor.

In various embodiments, the simulated bladder 44 is adhered to the simulated pelvic floor 31 at the pubis, and the simulated prostate 43 is adhered to the simulated endopelvic fascia sheet 41, anterior to the simulated rectum 53. The simulated seminal vesicles 45 are adhered only to the simulated prostate 43 and the simulated bladder 44. In various embodiments, the simulated prostate, simulated bladder, simulated seminal vesicles, simulated urethra and/or Toldt's/endopelvic fascia sheet are colored or otherwise distinguished from each other visually, e.g., colored, and/or tactilely, e.g., having different dimensions, thickness and/or length. In various embodiments, the simulated prostate, simulated bladder, simulated seminal vesicles and/or simulated urethra are all made of silicone.

In accordance with various embodiments, the colon/rectum assembly comprises a simulated colon 51 attached to a simulated rectum 53. The simulated colon is contoured or has curves, bumps or other surface features thereby distinguishing the simulated colon from the substantially smooth and tubular simulated rectum. The transition from the bumpy colon to the smooth rectum forms the recto-sigmoid junction, a visual landmark during surgery and provided in various embodiments of the surgical simulator. In various embodiments, a simulated parietal peritoneum 54 has a proximal end or portion attached to the simulated colon 51 and a distal end or portion attached to the simulated rectum 53. Additionally, the simulated parietal peritoneum 54 is attached to the Toldt's/endopelvic fascia sheet with portions of the mesentery/mesorectum assembly 55 disposed therebetween.

In various embodiments, a sheet of the same material used to create the simulated Toldt's/endopelvic fascia sheet 41 is cut and attached to itself and forms the simulated mesentery 57. In various embodiments, a simulated inferior mesenteric artery (IMA) 52 is attached to the simulated colon 51, e.g., at the proximal portion of the simulated colon and thus is only accessible and/or visible at the proximal portion of the TME surgical simulator.

In various embodiments, the mesentery/mesorectum assembly comprises a simulated mesentery 57 and a simulated mesorectum 58 and a simulated IMA 52 and inferior mesenteric vein (IMV) 56 is attached to the simulated mesentery 57. The simulated mesentery is attached to or integrated into the simulated parietal peritoneum 54 where the two interfaces. In various embodiments, the simulated mesentery 57 and simulated mesorectum 58 are a single monolithic structure with the simulated mesentery 57 being at the proximal portion of the TME surgical simulator and the simulated mesorectum 58 being at the distal portion of the TME surgical simulator. In various embodiments, a simulated IMA 52, IMV 56 and mesentery 57 are positioned at or in the proximal portion of the TME surgical simulator and thus is only accessible and/or visible at the proximal portion of the TME surgical simulator. In various embodiments, the simulated IMA and/or IMV are all made of silicone.

In accordance with various embodiments of the present invention, the first step of a simulated TME procedure using a laparoscopic approach is entry through the simulated parietal peritoneum. The root of the mesentery is a common point of entry and can be recognized by a color difference between the mesenteric fat and posterior abdominal wall. This entry point can also be recognized by observing movement in the anatomical layers when the sigmoid colon is moved with laparoscopic instruments, as well as by the identification of the bulge of the inferior mesenteric artery (IMA) through the mesentery and peritoneum. The identification of this anatomical feature can provide a necessary starting point for a TME procedure. Referring to the TME surgical simulator, the simulated parietal peritoneum 54 is adhered or otherwise attached to the simulated visceral peritoneum more securely than the simulated mesentery 57 to simulate realistic tenting and dissection. The simulated colon 51 in various embodiments is tubular and/or made of silicone. The simulated colon is adhered or otherwise attached on top of the simulated parietal peritoneum to simulate the descending colon. In various embodiments, the sheet thickness is increased or decreased and may be made with a lower or higher durometer material to change the elasticity and structure of the simulated mesentery. The simulated mesentery 57 in various embodiments is molded out of a conductive material to enable the user to use laparoscopic energy equipment to make incisions. The simulated mesentery is assembled such that it is adhered to the simulated Toldt's/endopelvic fascia layer 41 up to the simulated pelvic brim. As such, this allows abdominal dissection to be differentiated from the lower pelvic dissection that is performed from the laparoscopic approach to mobilize the rectum.

Once through the simulated parietal peritoneum 54, the surgeon can dissect through the simulated avascular plane, e.g., the simulated Toldt's/endopelvic fascia layer 41, to find the simulated IMA 52, IMV 56, aorta 33 and/or ureters 42. Ureter identification can be important to avoid surgical complications and further reinforce training and the effects of the simulation. Once the simulated structures are identified, the simulated IMA 52 can be skeletonized, ligated and divided close to the simulated aorta. In various embodiments, these simulated organ and/vascular structures, e.g., the simulated IMA, IMV, aorta and/or ureter, can be cut, stapled, sutured and tied to simulate ligation and division. The simulated ureters and aorta allow for the identification of the simulated IMA 52 and IMV 56 during the simulated TME procedure. In various embodiments, the simulated vasculature varies in thickness and can be hollow or hollow and fluid filled to simulate bleeding. One or more of the simulated vasculatures may also disposed within the surgical simulator without adhesion or minimal attachment, e.g., loosely, directly adhered or otherwise attached to a silicone structure and/or any combination thereof. Dissection is continued laterally toward the simulated abdominal sidewall mobilizing the simulated mesentery.

In various embodiments, the simulated avascular plane, e.g., the simulated Toldt's/endopelvic fascia layer, comprises a fibrous batting layer made of polyester fiberfill (polyfil). The tactile feedback of the fibrous layer, e.g., fibers within the batting, provides sufficient resistance to allow blunt dissection using laparoscopic instruments to be utilized. This dissection within the fibers allows the simulated vasculature within the layer to be skeletonized. Below or adjacent to the simulated Toldt's fascia is a thin layer relative to the simulated Toldt's fascia that represents the layer entering the retroperitoneum or visceral peritoneum. The thinness of or fragility of this layer (retroperitoneum/ visceral peritoneum) and by extension the simulated Toldt's/ endopelvic fascia layer 41 simulates the ease in which this plane can accidently be entered, which is a challenge encountered during the surgical procedure and provided or simulated by the TME surgical simulator. In various embodiments, the simulated Toldt's fascia is a fibrous layer or filling, e.g., batting, representing or simulating connective tissue and is disposed next to and/or attached to the simulated retroperitoneum or visceral peritoneum, e.g., one or more silicone sheets. The simulated Toldt's fascia and/or the simulated retroperitoneum or visceral peritoneum are disposed next to and/or attached to the simulated parietal peritoneum 54.

In various embodiments, the simulated Toldt's/endopelvic fascia layer 41 is a composite layer 41, for example, having fibrous material and silicone, including the simulated Toldt's fascia layer along with the simulated visceral peritoneum or retroperitoneum layer with the simulated endopelvic fascia layer being a continuation of the combined simulated Toldt's fascia layer and the simulated visceral peritoneum or retroperitoneum layer. As such, together, in various embodiments, the simulated Toldt's fascia layer and the simulated retroperitoneum or visceral peritoneum layer form a composite layer, e.g., fibrous material and silicone, and the simulated endopelvic fascia layer is an extension of this composite layer, being a continuation of the combined simulated Toldt's fascia layer and the simulated retroperitoneum or visceral peritoneum layer. In various embodiments, the simulated Toldt's fascia layer and simulated visceral peritoneum or retroperitoneum layer are disposed in the simulated abdominal cavity, and thus so named, while the simulated endopelvic fascia layer is disposed in the simulated pelvic cavity and thus so named differently. As such, reference to the simulated endopelvic fascia layer may be used interchangeability throughout the description with the simulated Toldt's/endopelvic fascia layer and vice versa. Similarly, the combined or composite layer of the simulated Toldt's fascia and simulated retroperitoneum or visceral peritoneum may be used interchangeability throughout the description with the simulated endopelvic fascia layer and simulated Toldt's/endopelvic fascia layer and vice versa.

In various embodiments, the retroperitoneum layer or portions thereof is yellow or otherwise discernible via color or the like to further distinguish or highlight the retroperitoneum layer. Within the simulated retroperitoneum layer, there are additional fibers or fibrous material, e.g., a batting layer (simulated Toldt's fascia), that contains the simulated aorta, nerves, and gonadal vessels. The simulated ureters and nerves are adhered or otherwise attached to the simulated retroperitoneum 41 while the simulated aorta 33 and gonadal vessels 32 are adhered or otherwise attached to the simulated pelvic floor. In various embodiments, the simulated pelvic floor 31 is a thin sheet molded out of pink or blood/flesh colored silicone. The simulated nerves 34, ureters 42 and gonadal vessels 32, in accordance with various embodiments, are adhered or otherwise attached to the respective simulated sheets or layers at an angle, slant or similar orientations such that the simulated vasculature pairs are closer to each other at the proximal end than at the distal end of the respective simulated sheets or layers. As such, in the simulated lower pelvic region, when the simulated ureters and gonadal vessels are wrapped around the simulated mesorectum 58, the simulated vasculature meet at the location of the simulated bladder 44 and prostate 43.

To further simulate the appearance of the abdominal cavity under the simulated retroperitoneum, in various embodiments, an additional pink silicone layer making up the simulated pelvic floor is placed under the simulated aorta and batting layer of the simulated retroperitoneum. This allows the visualization of the color of the simulated abdominal cavity when the simulated retroperitoneum layer is encountered.

In accordance with various embodiments, the silicone and fibrous layers that make up the simulated mesentery, Toldt's fascia, endopelvic fascia, and/or retroperitoneum are adhered using silicone. Silicone adhesive or alternative adhesives such as cyanoacrylate adhesives and rubber cement in various embodiments are used to adhere the layers together. When using silicone layers, the silicone can be readily masked within the silicone layer and application quantities can be easily controlled with syringes and sponge like materials, such as polyurethane foam. It also creates a strong silicone to silicone bond while also adhering to the fibrous layers, if any is present. The silicone to silicone bonds between the silicone mesentery and the fibrous material and between the fibrous material and the silicone retroperitoneum layer allow the dissection to be contained within the fibrous material, e.g., the batting layer. Similarly, in various embodiments, silicone to silicone bonds between the silicone retroperitoneum layer and the fibrous layer and between the fibrous layer and a red silicone layer allow the dissection to be contained within the fibrous material, e.g., the batting fibrous layer.

In accordance with various embodiments, to simulate the difference in dissection within the simulated Toldt's/endopelvic fascia layer 41, the amount of adhesive, silicone, and/or pressure are used and varied. Additionally, various durometers of silicone are used to change the way in which two parts made of silicone adhere together and tear or pull apart. This simulates different techniques of blunt dissection useful in different areas of the anatomy. Within the Toldt's/ endopelvic fascia sheet 41, in accordance with various embodiments, more adhesive is used relative to the simulated retroperitoneum layer. As such, this provides tactile feedback of the more difficult dissection within the correct plane, the Toldt's/endopelvic fascia sheet, versus the easier, looser dissection of the wrong plane, into the retroperitoneum. It should be noted that staying within the correct dissection layer between the Toldt's/endopelvic fascia layer 41 and the mesentery/mesorectum layer 57, 58 avoids surgical complications, as the dissection within simulated retroperitoneum layer and pelvic floor 31 leads to simulated anatomical structures, within the simulated lower pelvis, that can be damaged during the simulated surgical procedure.

In accordance with various embodiments, the fibers or fibrous material attached or incorporated into the layers, e.g., within Toldt's/endopelvic fascia layer 41 and/or the retroperitoneum sheet, can include other low tear strength materials. These materials can be or also include but are not limited to gel like materials and soft conductive materials on which electrosurgical energy can be used. Using fibrous materials, such as batting and the like, also enhances the simulation providing a visual appearance of the fibers, which is observed in the simulated surgical procedure.

In various other embodiments, the fibrous or fiber like material is not included or otherwise integrated into the various simulated layers or sheets, thus creating direct contact between sheets or layers of material within the surgical simulator. In such embodiments, distinction between the various layers is indicated by color versus varying textures and materials. These various embodiments or combinations thereof however can create added difficulty to the simulated procedure performed in the simulated TME surgical simulator due to unrealistic visual feedback.

In accordance with various embodiments, the molding or forming of silicone sheets including fibrous material, e.g., batting, to extend among or from or appear between the simulated tissue layers creates a plane of dissection in which a user must remain while completing simulated dissection down the simulated pelvis similar to fully simulate dissection. This further allows for an enhanced and/or realistic margin for error. Additionally, in various embodiments, the fibrous silicone composite material provides similar tactile and visual feedback during the simulated procedure and can be manipulated during manufacturing to change the level of difficulty of the simulated procedure.

In accordance with various embodiments, simulated dissection of Toldt's/endopelvic fascia layer 41 is continued medial to lateral towards the left sidewall of the frame in order to mobilize the simulated left, descending colon and sigmoid colon so that the simulated dissection within the simulated lower pelvis can occur. The descending and sigmoid colon are then freed from the sidewall of the frame by dividing the white line of Toldt. In accordance with various embodiments, the adhesion line along the left sidewall resembles the white line created by the junction of two tissue planes.

Once the simulated descending colon and sigmoid colon are mobilized, posterior dissection into the simulated pelvis continues. Within the surgical simulator, in various embodiments, the simulated sigmoid colon passes through the silicone layer that covers the frame simulating the pubis. At the pelvic brim, a specific aspect of the TME procedure is that the surgeon remains in the correct dissection plane between the simulated colon/mesorectum and the simulated Toldt's/endopelvic fascia layer 41, an area between two tissue planes known as the holy plane 71. During this simulated posterior dissection, the surgeon can recognize landmarks, such as simulated nerves 34, to ensure they are on the right path of dissection.

Since it is the same set of layers in the surgical simulator that comprise the circumferential dissection layers around the mesorectum and colon at the posterior end, the same adhesion properties between the layers apply. As such, dissection through the holy plane is more difficult or notable when compared to the dissection through the wrong plane. Furthermore, in various embodiments, adjusting the amount of fibrous material can make the simulated procedure more challenging. In various embodiments, the added fibrous material or batting strengthens the thin silicone sheets it is added to and eases manufacturing when adhering the simulated layers together. The simulated Toldt's/endopelvic fascia layer 41 continues posteriorly within the TME surgical simulator to make up the outer boundary of the holy plane. Circumferential dissection around the simulated mesorectum and colon is simulated through the dissection of the fibrous material simulating the holy plane. At the posterior side of the colon 51, within the retroperitoneal space is a pair of silicone molded thin branched structures to simulate nerves, a landmark for the TME procedure. In various embodiments, the simulated nerves 34 are colored, e.g., white, in order to be visualized through the thin yellow silicone layer of the simulated retroperitoneum. The placement of the nerves within this simulated retroperitoneal space reflects the anatomical placement of the nerves. Dissection within the retroperitoneal space within the surgical simulator would allow the simulated nerves 34 to be encountered in this plane, which would be indicative of the dissection in the wrong plane.

In accordance with various embodiments, in the TME surgical simulator, the Toldt's fascia/retroperitoneum layer and the endopelvic fascia layer are all integrated and/or one in the same. In accordance with various embodiments, in the TME surgical simulator, three main simulated tissue planes or layers are provided, the simulated mesentery/mesorectum layer, the Toldt's fascia/endopelvic fascia/retroperitoneum layer and the pelvic floor/sidewall/peritoneum layer. These tissue planes should not be confused with the two major planes of dissection, the holy plane 71, which occurs between mesentery/mesorectum 57, 58 and Toldt's/visceral peritoneum/endopelvic fascia layer 41 ("Toldt's/endopelvic fascia") and the wrong plane 73, which occurs between Toldt's/visceral peritoneum/endopelvic fascia ("Toldt's/endopelvic fascia") and the pelvic sidewall layers.

Dissection into the wrong plane can cause complications, such as issues with the presacral veins or penetration of the mesorectal envelope resulting in an incomplete mesorectal dissection. By providing recognizable landmarks, such as nerves, bladder, prostate and seminal vesicles, the surgical simulator ensures or assists the surgeon or user to not dissect into the wrong plane. In accordance with various embodiments, within the simulated TME surgical simulator, the simulated nerves 34 are positioned on the posterior side of the mesorectum and colon and dissection within the plane containing the nerves is indicative of dissection within the wrong plane. Additionally, in various embodiments, the looser tactile feedback of and easier dissection through the simulated layers is a second indicator of dissection within the wrong plane. Continuation of the dissection within this plane to the anterior side of the colon, towards the simulated pubis will lead to simulated structures of the prostate 43, seminal vesicles 45, and bladder 44. The simulated prostate 43 and seminal vesicles 45 in various embodiments are cast using silicone or urethane foam and colored, e.g., pigmented blue and white, respectively, to enhance the simulation or correspond with the anatomical structures they represent. A simulated bladder 44, in various embodiments, is made of silicone and the simulated seminal vesicles are placed on either side of the simulated bladder. In various embodiments, the simulated prostate comprises a silicone molded simulated urethra 46 resting underneath or extending there through. These simulated structures in various embodiments are disposed within the frame such that they reflect their anatomical position relative to the simulation.

In various embodiments, adhesives such as silicone adhesives or cyanoacrylate adhesives can be used to adhere the simulated components together. Additionally, in various embodiments, gel, rubber, foam, and urethane materials can be used in the simulated components. In various embodiments, silicone, silicone foams, and urethane foams have desirable material properties to simulate the visual appearance and tactile feel, shape, and structure of the simulated components. The simulated anatomical structures, in accordance to various embodiments, during assembly, are adhered on top of the layer that make up the retroperitoneum at the posterior end and are surrounded on either side as well on top by fibrous material, e.g., batting, that makes up the retroperitoneal layer on the posterior end. Entrance into this wrong plane within the surgical simulator would be the result of dissection through the thin yellow layer that makes up the retroperitoneum on the posterior end.

In various embodiments, specific or particular adhesion or otherwise attachment patterns are used along the simulated mesentery and simulated organ structures to ensure relevant simulated anatomical interfaces are provided. Variations to the way in which anterior dissection can be simulated, in accordance with various embodiments, includes the usage of silicone, foam and/or fibrous material to create thicker or thinner planes of dissection to decrease and/or increase the level of difficulty of the simulated procedure respectively. Furthermore, assembly of these materials can vary in relative distance from other simulated planes and layers to provide a varying working space during the simulated TME procedure. In accordance with various embodiments, the TME surgical simulator creates a challenging surgical environment in which room for error is provided, encouraging the development of manual dexterity and the anatomical and surgical knowledge required to successfully perform and assess the performance of the simulated TME procedure. Moreover, strategic placement of attachment points or areas creates visual and tactile feedback during a simulated anterior dissection.

In accordance with various embodiments, simulated tissue structures can be molded out of conductive materials, which utilize visual indicators such as color as opposed to utilizing visual indicators of texture. Thus, dissection in the wrong plane can be identified by changes of color upon entrance into the various simulated tissue layers. In various embodiments, the simulated dissection in the wrong plane involves incorporation of structural supports in the surgical simulator's frame to widen the lateral sides of the colon/rectum assembly. This can further simulate the easier dissection encountered in the wrong plane of dissection, and can also serve as providing additional simulated insufflation, i.e., providing the surgeon with a larger simulated surgical work space. These structural supports in various embodiments are made of hard plastics or soft materials such as silicone, which create strong adhesion points with other simulated tissue structures.

The TME surgical simulator in accordance with various embodiments provides adequate visual and tactile feedback to the surgeon during the simulated procedure. Moreover, the TME surgical simulator can be altered to adjust the difficulty of simulated dissection provided by the simulator.

To meet clinical needs, the level of difficulty of the simulated TME procedure can be adjusted, for example, by increasing or decreasing the amounts of fibrous tissue, adhesive and/or silicone material.

Simulated dissection from the laparoscopic approach is performed to create a circumferential dissection around the mesorectum. This dissection is performed within the holy plane to free the fatty mesorectal envelope from surrounding structures. Circumferential mobilization of the mesorectum is continued to the pelvic floor where the rectum is divided at its distal end. Due to the curve of the sacrum, visualization of the dissection from the laparoscopic end is limited; therefore, a transanal approach can be used to create the circumferential dissection around the mesorectum. The dissection from the transanal end and laparoscopic end can allow for the complete mobilization of the colon. The colon is then transected proximally before the specimen is removed. After removal, the specimen is evaluated for tears in the mesorectal envelope and for any exposure of the rectal wall. A complete dissection will exhibit a smooth surface with the entire outer envelope and contained volume of filling of the mesorectum intact.

In various embodiments, the simulated mesorectum structure is made of soft silicone and gel like materials. The posterior side 64 of a balloon or envelope formed from the simulated mesorectum structure is larger than the anterior side 63 and/or both the proximal and distal end taper, with a more obvious taper at the distal end. The simulated mesorectum structure, in various embodiments, includes an outer membrane, making up the balloon, with the balloon or envelope simulating the fascia propria surrounding a fatty envelope. This membrane in various embodiments is a thin, fragile balloon layer and is made up of a silicone and fibrous material composite to allow additional silicone layers to be adhered circumferentially using silicone as adhesive. The mesorectum fatty fill in various embodiments is gel-like, soft and/or fluid enough that it can partially escape or exit from the outer membrane upon a puncture or cut and yet still have the ability to maintain its shape within the simulated mesorectum balloon envelope in such a way that it simulates the anatomical mesorectum once it has been punctured. Furthermore, the simulated specimen is fragile enough to be accidentally breached by laparoscopic scissors, graspers, or dissectors during the simulated division of the distal end of the colon and mesorectum for removal of the specimen. In various embodiments, due to the consistency and/or amount of the fatty fill filling the simulated mesorectum/mesentery, the excised simulated mesorectum specimen will have visual voids or lumps indicative of where materials have leaked out. The fibrous material creates structure within the gel material such that it prevents an unrealistic ejection of the gel from any given puncture site. Therefore, the simulated specimen can be graded and assessed. Grading of a simulated specimen can be assigned on a 1-3 scale where 3 is a complete dissection, where the simulated mesorectum is intact without any punctures and/or tears, 2 is an incomplete dissection with minimal tears and/or punctures and 1 is an incomplete dissection with punctures, tears and exposure of the rectal wall.

In various embodiments, the simulated mesorectum structure is filled with a fatty fill 61, such as soft or dense foam, silicone, conductive materials, gelatin and various gels such as Kraton. The simulated specimen may have the thin outer membrane, or the outer membrane may be made of a gel, conductive material, or foam or if the simulated mesorectal structure has the strength to hold its shape, the simulated specimen may have no outer layer.

In various embodiments, the simulated mesorectum may not simulate tissue properties but rather is graded by color patterns and markings made on the simulated specimen during the simulated dissection. Such embodiments can include a molded component, which resembles the shape of the mesorectum made of foam, silicone or another soft material in a color. This molded component can be tightly wrapped or coated with a silicone sheet in a contrasting color. In various embodiments, if the simulated specimen is punctured during simulated dissection, exposure of the component color can indicate a tear or puncture.

The simulated mesorectum in accordance with various embodiments provides the user when performing the simulated TME procedure, realistic tactile and visual feedback along with an ability to assess their surgical technique. Furthermore, the simulated mesorectum can be graded upon removal similarly to that of a specimen removed from a patient. Furthermore, the simulated mesorectum in various embodiments is made with an outer silicone sheet, which enables adhesion to the other silicone and fibrous components within the TME surgical simulator.

According to various embodiments, anterior dissection of the mesorectum is simulated by creating various planes made of thin silicone sheets and fibrous material, e.g., batting. The simulated mesorectum and simulated mesentery 57, 58 are a continuous structure and are distinguished from the surrounding tissue by color and texture. The sheets that make up the envelope of the mesorectum and mesentery in various embodiments are similar in color to the surrounding tissue. In accordance with various embodiments, the mesentery and mesorectum are filled with a fatty fill 61, e.g., a yellow gel substance that simulates fat. The presence of this yellow gel behind the silicone envelope that forms the outer boundary of the mesentery and mesorectum gives these structures their color. Simulated dissection in the correct planes is identified by simulated anatomical landmarks such as the bladder, seminal vesicles, prostate and ureter. These simulated organ structures in various embodiments are made of silicone and foam materials. The simulated mesorectum 58, mesentery 57, bladder 44 and ureters 42 are assembled in such a way that allows the surgeon to identify these useful landmarks in order to complete the simulated TME procedure. In various embodiments, circumferential dissection of the mesorectum within the correct plane of dissection, the holy plane, is simulated by creating a cylinder made of a thin silicone sheet and batting composite. This thin silicone sheet has been previously described as the simulated retroperitoneum in which a thin layer of fibrous material, such as batting, has been adhered to it to simulate the holy plane of dissection. In various embodiments, the simulated mesorectum and the thin sheet of silicone creating the simulated retroperitoneum, which is named the wrong plane in the lower pelvis, are distinguished by color and texture as well as the simulated holy plane, which lies in between and divides into two, indicating the correct path of simulated dissection circumferentially around the simulated mesorectum. Location of landmarks such as nerves, ureters, and gonadal vessels, are useful for this dissection aspect the simulated TME procedure and are identified as being below the retroperitoneum. The inclusion of simulated nerves 34 and ureters 42 adhered or otherwise attached to the posterior of the simulated Toldt's/endopelvic fascia layer 41 allow surgeons to confirm they are dissecting in the correct plane.

The simulated Toldt's/endopelvic fascia layer 41 forms a tissue plane around the mesorectum 58 and in various embodiments with strategic placement of adhesive, silicone and/or other similar attachments ensures proper visualization of relevant simulated landmarks. In various embodiments, variations to the way in which circumferential dissection is simulated includes the usage of more or less silicone, foam or batting material to create thicker or thinner planes to decrease or increase the level of difficulty of the simulated procedure respectively. The addition of adhesive, more silicone adhesion and/or similar types of attachments of the simulated Toldt's/endopelvic fascia layer 41 to the simulated mesorectum 58 can also be used to create a more challenging circumferential dissection through the holy plane. In various embodiments, the difficulty of dissection in the holy and wrong planes of dissection can also be adjusted by altering the amount of pressure used to glue the planes together. Additionally, the difficulty of dissection in the holy and wrong planes of dissection can be adjusted by changing the size of the tissue planes relative to the next outer plane. For example, by making the overall surface size of the Toldt's/visceral peritoneum/endopelvic fascia ("Toldt's/endopelvic fascia") layer smaller relative to the pelvic floor layer, the dissection through the wrong plane of dissection that exists between Toldt's/endopelvic fascia and pelvic sidewall becomes easier, because there is more outward stretch or tension in the Toldt's/endopelvic fascia layer, and thus more force pulling that layer inward as the user dissects into the pelvis.

By varying the amount and/or type of fibrous material and/or attachment, e.g., silicone adhesive, pressure or the like, and/or any combination thereof, the difficulty of dissection in the holy and/or wrong plane can be controlled and/or varied. It should be noted however that such adjustments or variations may distract or alter the tactile and/or visual feedback of the surgical simulator. As such, a balancing of fibrous material and/or attachments can be required or adjusted to appropriately provide the desired dissection difficulties or challenges and visual/tactile feedback. It should also be noted that the depicted holy and/or wrong planes are exaggerated in size, shape, uniformity and/or openness, to ease depiction and readability of the description. Fibrous material, adhesive and the like, for example, would extend or otherwise occupy all or portions of the dissection planes. The dissection planes become pronounced or otherwise separated during simulated dissection of the surgical simulator.

In various embodiments, use of a conductive material for the simulated mesorectum 58 and Toldt's/endopelvic fascia layer 41 can allow for the use of energy during this segment of the simulated TME procedure. Furthermore, assembly of these materials could vary in a way such that the relative distance from other simulated planes and tissues will provide a larger or tighter workspace during the simulated TME procedure. Furthermore, the outward tension that results from stretching and attachment of the various layer or assemblies simulates the effects of insufflation on dissection in the pelvic cavity. Due to insufflation being used in the real procedure, when the surgeon performs circumferential dissection around the mesorectum within the pelvic cavity, the pressure from the insufflation gas tends to pull the tissue planes apart as the surgeon makes cuts and bluntly dissects within the dissection plane.

Additionally, in this surgical simulator the adhesion of the silicone simulated mesorectum to the simulated silicone visceral peritoneum layer via the batting layer provides room for puncturing and tearing of the simulated mesorectum that cannot be achieved with usage of varying materials that do not adhere to silicone.

In various embodiments, there is a pronounced shape of the simulated mesorectum 58 where it is curved and more voluminous on the posterior side following the curve of the sacrum while remaining thinner on the anterior side towards the pubis. In various embodiments, the transanal approach for the simulated TME procedure can be used to mobilize the rectum and mesorectum in the low pelvis region. In this approach, the surgeon uses a transanal access system, platform and/or channel to access the rectum, create a purse string and occlude the rectum. A circumferential incision is made around the purse string to gain entry into the holy plane. Entry into the holy plane from the transanal approach requires a great deal of skill and anatomical knowledge. In various embodiments, a simulated transanal adapter is used to gain entry into the simulated rectum. The transanal adapter allows for the surgical simulator the interface to a simulated laparoscopic trainer. The adapter contains a rigid component that locks into the top and bottom torso of the trainer. The rigid component can be made of urethane or plastic. Molded into the adapter is a soft silicone layer that contains a small opening that simulates the anus in which the access platform can interface with. Variations in materials to simulate the anus and flesh around the adapter can include soft rubber like materials or rigid materials. The use of the soft materials allows the flexibility and ability to manipulate access instruments within the simulated orifice. In various embodiments, the use of silicone allows a strong silicone to silicone bond to be used when interfacing with additional silicone components found within the simulated TME surgical simulator.

In accordance with various embodiments, at the distal end of the simulated TME surgical simulator, the simulated rectum 53 extends beyond the frame such that it can be placed around the access channel that is penetrated through the orifice of the adapter described above. The diameter of the rectum, in various embodiments, is smaller than the access channel to allow the rectum to be stretched around the channel and remain secure. In various embodiments, the simulated rectum can be directly adhered or otherwise directly attached to the silicone portion of the adapter. As such, the access channel would be inserted through both the adapter and colon simultaneously, which could be challenging for a user due to the difference in size that allows the tight interface fit. The extension of the rectum at the distal end beyond the frame of the surgical simulator and beyond the circumferential dissection layers provide sufficient length for the access channel to remain in place. In various embodiments, the frame and/or the dissection layers can extend to be adjacent with the adapter. This in turn would cause the surgical simulator at the distal end to become stiffer and less mobile, which is unrealistic to the anatomy.

Once the access channel is placed, the inner lumen of the simulated colon is encountered, and the laparoscopic instruments can be used to create a purse string. In various embodiments, mesh can be embedded within the simulated rectum 53 to increase or enhance its tear strength enough to withstand forces generated by suturing. In various embodiments, additional material is used to simulate the rectum, enhancing its strength to hold a suture without the use of mesh and/or in combination with the mesh. The additional materials can include silicone, Kraton, other rubber like materials, and/or combinations thereof. Once a purse string is created, the inner lumen of the simulated colon is occluded, exposing the circumferential dissection layers around the rectum.

In accordance with various embodiments, at the distal (anal) end, the rectum is followed by the mesorectum fatty fill 61, which is encased within a silicone envelope, and the outermost layer of the mesorectal silicone balloon or envelope is adhered or otherwise attached to the Toldt's/endopelvic fascia sheet or layer. The plane of dissection between the envelope of the mesorectum and endopelvic fascia represents the holy plane. The simulated endopelvic fascia sheet 41, in various embodiments, is a thin yellow layer that is called the retroperitoneum in the pelvic cavity during the simulated laparoscopic approach. Between the endopelvic fascia and pelvic sidewall is another layer of fibrous material, which creates or represents the wrong plane of dissection. Around this fibrous layer is a pink silicone layer to visually represent the pelvic floor/pelvic sidewall. The layers are adhered or otherwise attached together, such that upon placement of the purse string, the simulated rectum and mesorectum cinch in such a way that access to the correct (holy) and incorrect (wrong) planes 71, 73 for simulated dissection are allowed. These planes of dissection occur between the mesorectum and endopelvic fascia and between the endopelvic fascia and pelvic sidewall. During simulated circumferential dissection of the simulated mesorectum from the transanal entry, the wrong plane 73 can easily be entered due to the cinching of a culmination of the surgical simulator's simulated planar tissue layers at the distal end of the mesorectum. This creates a confined work environment thereby simulating that, which could be found in a patient. The wrong plane may be entered from the transanal approach and entry into the wrong plane can be visualized by color and texture change, as well as the tactile feedback between the ease of the dissection between the planes. The holy plane has a more difficult and/or tactile response in comparison to the dissection through the wrong plane. In various embodiments, this haptic feedback response is simulated through the variation in adhesion or attachments between the fibrous layers extending into or between the planes.

In accordance with various embodiments, entry via the transanal approach may vary in the shape of the simulated pelvis structure, which can be altered to create a smaller or larger work environment and/or changing the proximity of the simulated tissue layers, and landmarks can also alter the level of difficulty of the simulated TME procedure. In various embodiments, simulated entry via the transanal approach may further involve incorporation of additional structural supports in the frame to enable improved tissue structure interface and simulated insufflation, providing the surgeon a greater amount of simulated surgical workspace. These structural supports, in various embodiments, may be made of hard plastics or soft materials such as silicone, which create strong adhesion points with other simulated tissue structures, made of silicone. The simulated transanal entry of the TME surgical simulator in accordance with various embodiments provides adequate challenge in completion of the simulated TME procedure by creating a confined work environment that resembles the confined space found within a pelvic cavity, and allows room for entrance into the wrong plane, which is a learning objective for a TME procedure. Moreover, the simulated rectum 53 holds the purse string long enough for the surgeon to occlude the rectum and enter the holy plane. In various embodiments, the simulated mesorectum at the transanal end of the TME surgical simulator is tapered to resemble or simulate the taper of the mesorectum in a patient. In various embodiments, the simulated mesorectum 58 does not have a taper at the transanal end but resembles or simulates the bulge of the mesorectum as found in a patient. In a similar variation, the mesorectum can encapsulate the rectum at the same thickness from end to end of the fatty envelope. In various embodiments, the taper at the transanal end of the mesorectum allows access into the holy plane within the tight workspace of the transanal end of the surgical simulator, while also providing the ability for the user to enter the wrong plane if they are too aggressive in their dissection.

Figure 18:
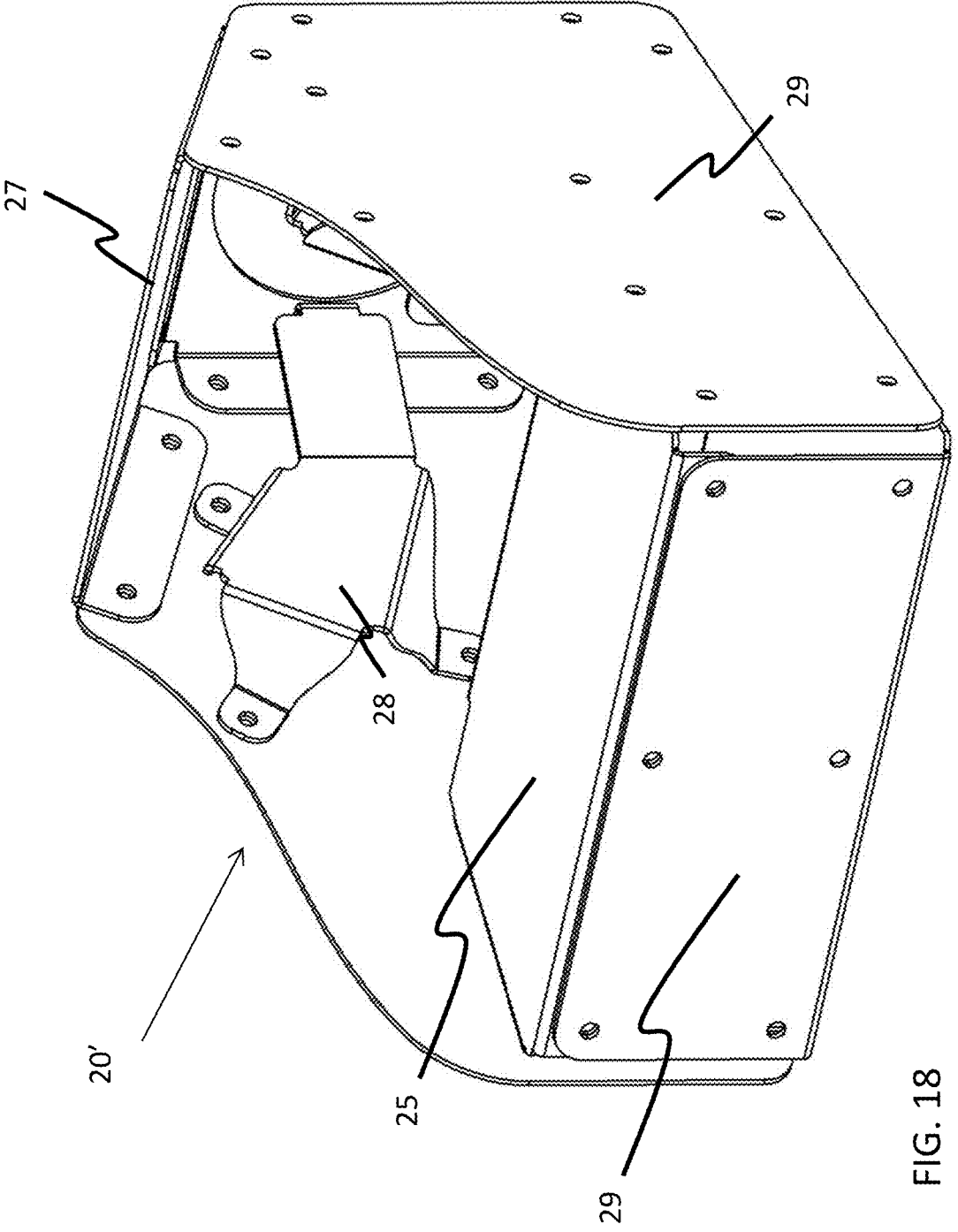
FIG. 18 is a perspective view of a frame of a surgical simulator in accordance with various embodiments of the present invention.
Figure 19:
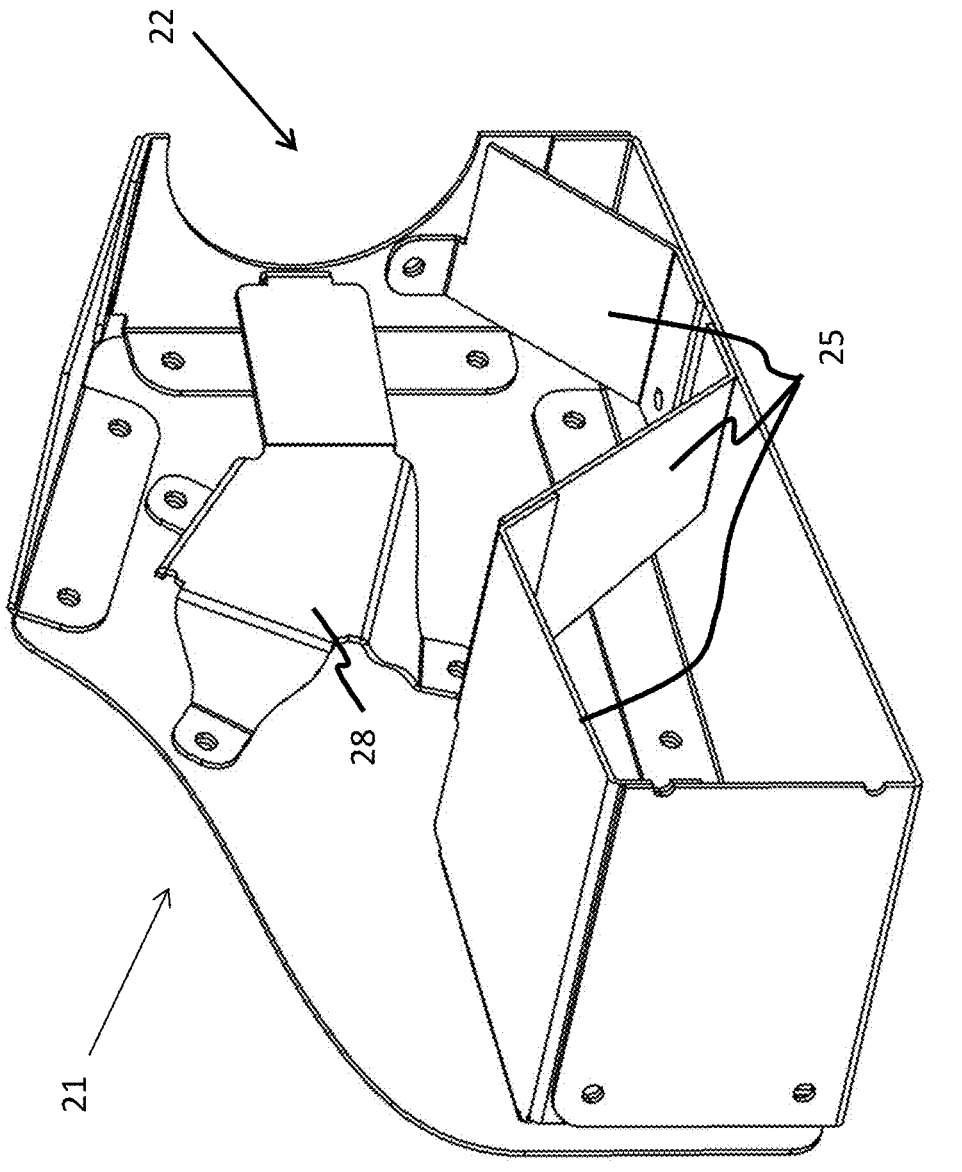
FIG. 19 is a perspective cross-sectional view of a frame of a surgical simulator in accordance with various embodiments of the present invention.
Figure 20:
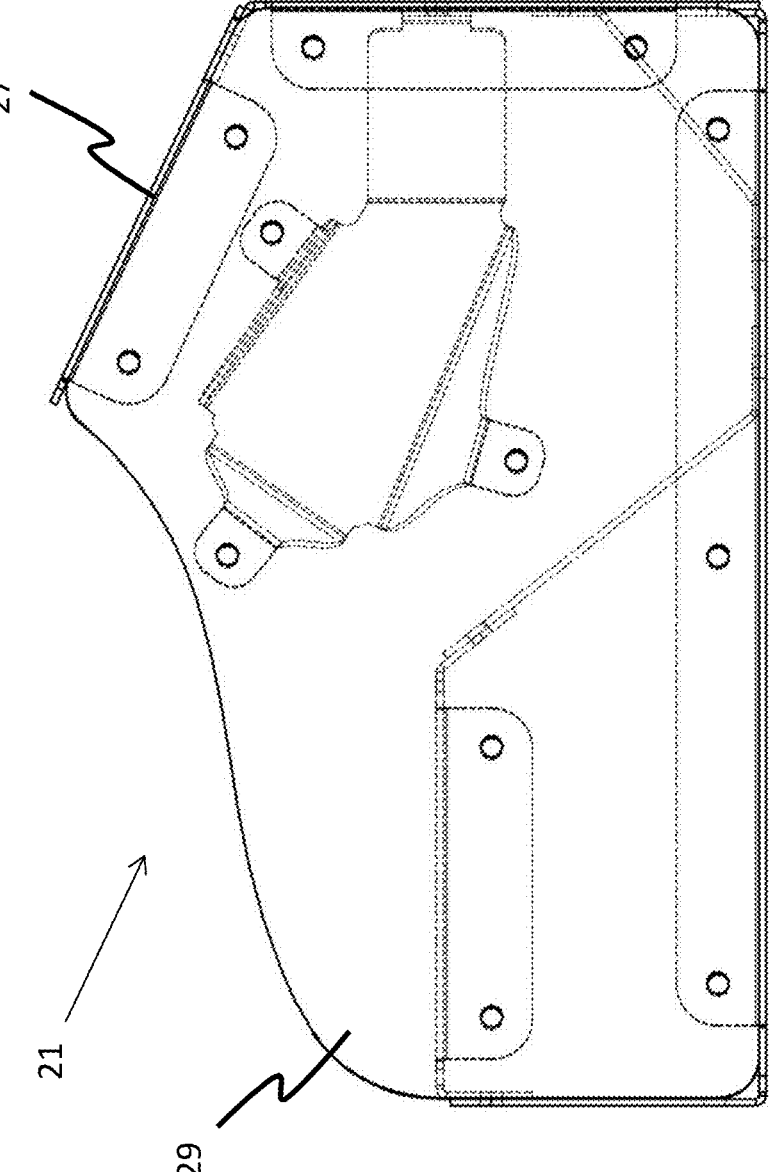
FIG. 20 is a side view of a frame of a surgical simulator in accordance with various embodiments of the present invention.

The narrow pelvis in male patients can pose a challenge for surgeons to reach the pelvic floor from a laparoscopic approach after complete circumferential dissection of the mesorectum. As such, in various embodiments, the TME surgical simulator provides a simulated pelvis structure, e.g., the frame/housing 20, 20', that supports the simulated tissue structures and creates a confined work environment, which simulates the natural curves of the pelvis. In various embodiments, as shown in FIGS. 18-20, the frame 20' comprises plastic sheets 29 cut, folded and assembled and in various embodiments in such a way that they resemble the deep sacrum curve of the pelvis. This curve creates limited visualization during dissection, thus provides another simulated feature in the TME surgical simulator. The plastic sheets, in various embodiments, are interfaced with thick silicone sheets through apertures in the frame sheets. These silicone sheets do not serve as anatomical features, but rather are used to secure simulated tissue structures, e.g., silicone tissue components, to the plastic frame components. In various embodiments, silicone is used to adhere the silicone tissue structures to the silicone sheets interfaced with the frame components forming durable silicone bonds that enhance or strengthen the TME surgical simulator. Similarly, simulated tissue structures, in various embodiments, are also adhered or otherwise attached to domed fixtures 28 that are then fastened or otherwise attached to the frame providing tension for the simulated tissue structures. Outward extension, stretch and/or tension, e.g., circumferential tension, of the simulated tissue can further simulate insufflation provided during laparoscopic procedures.

During surgery, insufflation gas stretches out the tissue planes within the patient. Thus, when the surgeon makes cuts in the tissue, the tension created by the insufflation gas makes the tissue planes pull away from each other. This is especially evident as the surgeon moves from the abdominal cavity to the pelvic cavity. This is also part of the reason why it is so easy to enter the wrong plane of dissection, and to continue in the wrong plane as dissection is continued into the pelvis. As such, in various embodiments, simulated tissue structures within the TME surgical simulator, especially within the pelvic cavity, are placed under circumferential tension as a way to simulate the behavior of tissue planes that are under tension as a result of insufflation.

In various embodiments, the frame is made of thin plastic sheets that adds flexibility and enables formation of the curvature of the simulated pelvis without the need of additional bends, cuts, sheets and fasteners. Additionally, in various embodiments, the silicone sheets used for assembly may be adhered to the frame with adhesive and/or fasteners. In accordance with various embodiments, the frame provides a confined and challenging work environment including limited visibility during posterior dissection through the holy plane. Moreover, in various embodiments, the frame creates supports that can be utilized to provide simulated insufflation to the surgical simulator as well as manipulate the level of difficulty of the surgical simulator by widening or narrowing the work environment. In various embodiments, the modularity of having the frame be assembled by at least two pieces or components facilitates the assembly of the TME surgical simulator.

In various embodiments, the TME surgical simulator final assembly begins with the colon/rectum/mesentery/mesorectum assembly, which is the most interior assembly in the TME surgical simulator. Toldt's/endopelvic fascia assembly is attached around the mesorectum/rectum assembly, then the prostate assembly is added, and then the pelvic floor is attached to/around the toldt's/visceral peritoneum/endopelvic fascia. After the soft layers have been adhered or otherwise attached in place around the mesorectum, plastic/silicone components that interface the soft subassembly to the frame are attached in place to the final soft subassembly. The silicone subassembly is such that its outer surface is slightly smaller than the inner surface created when then plastic frame components are finally assembled. This size mismatch between the layers in the silicone subassembly and plastic frame results in circumferential tension of all tissue layers within the pelvic cavity of the surgical simulator. In various embodiments, this circumferential tension is the feature of the surgical simulator that provides simulated insufflation further enhancing the realism of the simulation.

In accordance with various embodiments, the TME surgical simulator assembly begins with a fully assembled frame 20' or a single monolithic frame 20. The pelvic floor/sidewall assembly adhered or otherwise attached into the frame. The Toldt's/visceral peritoneum/endopelvic fascia ("Toldt's/endopelvic fascia") layer is adhered or otherwise attached to the pelvic floor/sidewall and the mesorectum/mesentery/colon/rectum assembly is adhered or otherwise attached within the Toldt's/endopelvic fascia layer 41. When attached in such a fashion, each successive layer is under outward tension. This outward tension causes the layers or subassemblies to pull away from each other when dissection occurs between the layers, which create a realistic simulation of what occurs in a patient during laparoscopic dissection due to tension created by the insufflation gas.

In accordance with various embodiments, outward circumferential tension is achieved when the frame is formed with the simulated assemblies, e.g., the simulated mesorectum 58 or endopelvic fascia layers 41, already adhered to one another, with portions of the frame attached to the outermost layer of the simulated assemblies. The frame being larger than the simulated assemblies or layers causes the simulated layers to stretch as the frame is assembled or formed. This stretching that occurs during frame assembly provides this outward tension on the attached simulated tissue assemblies. This outward tension simulates insufflation without the use of insufflation gases or a sealed enclosure.

As a result of this pre-created or initially created outward tension, as the simulated dissection occurs, the corresponding simulated assemblies or layers tend to separate simulating the effects of insufflation. For example, during the simulated dissection, the outer layer or layers being attached to the frame remains fixed or tends to move outward or away from the inner layer or layers due to the release of the weight of the inner layer, the retraction or tendency of the material to move towards the frame and/or combination thereof. The inner layer, being separated from the outer layer, is released from the outward tension and thus moves or tends to move inward or away from the outer layer. The weight of the inner layer, the retraction or tendency of the material to return to a non-tension or pre-stretch state and/or a combination thereof can further cause the inner layer to move away from the outer layer.

In various embodiments, the pre-created outward tension is formed as each simulated assembly or layer is formed. For example, each simulated assembly is subjected to outward tension as it is attached to the frame or the preceding simulated layer between it and the frame. As such, each simulated assembly is pre-stretched and then attached to the preceding simulated layer or frame. Thus, tension is added to the simulated assembly or layers as these layers are added to the surgical simulator, resulting in the layers being less stiff, destructive when separated and/or overly adhered or attached to the other simulated layers or frame. In this method, glue and pressure are applied to the layers while they are pre-stretched, although glue and pressure quantities can be controlled independently of the layer size, and all characteristics, along with batting quantity, must be in balance to achieve the desired dissection qualities.

In various embodiments, the fibrous material can be thicker or thinner to affect dissection and overall tactile feel of the surgical simulator. The simulated assembly, e.g., the endopelvic fascia layer, includes wet silicone layers, one or more layers providing a waterproof barrier and one or more layers providing a bond with the fibrous material, and can also be made thicker. Making the silicone layer or layers thicker can make simulated dissection easier, as it becomes more difficult to damage or mishandle the simulated assembly with surgical instruments. Additionally, making the silicone thicker can increase the outward tension compared to a thinner layer of the same size and shape.

Figure 11A:
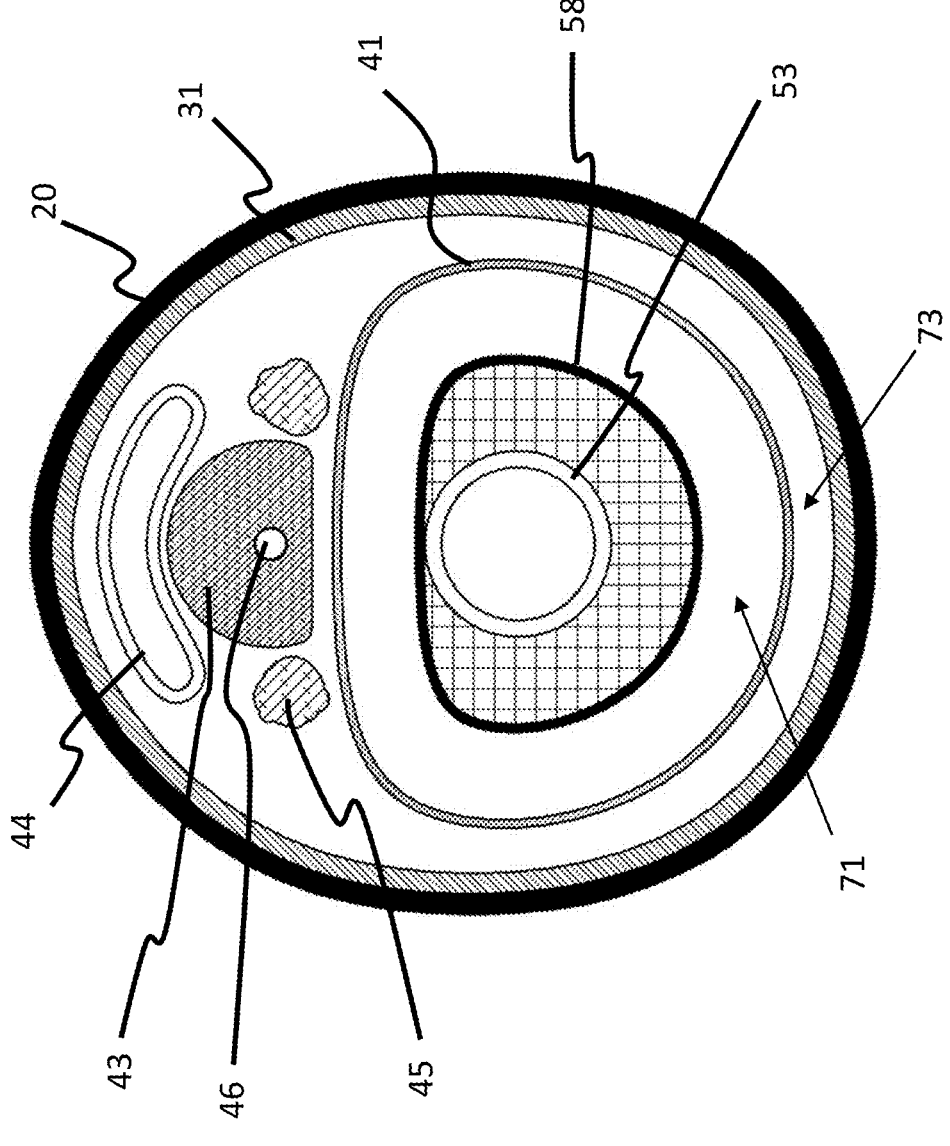
FIGS. 11A-11B are front cross-sectional semi-schematic diagrams of various configurations of a surgical simulator in accordance with various embodiments of the present invention.
Figure 11B:
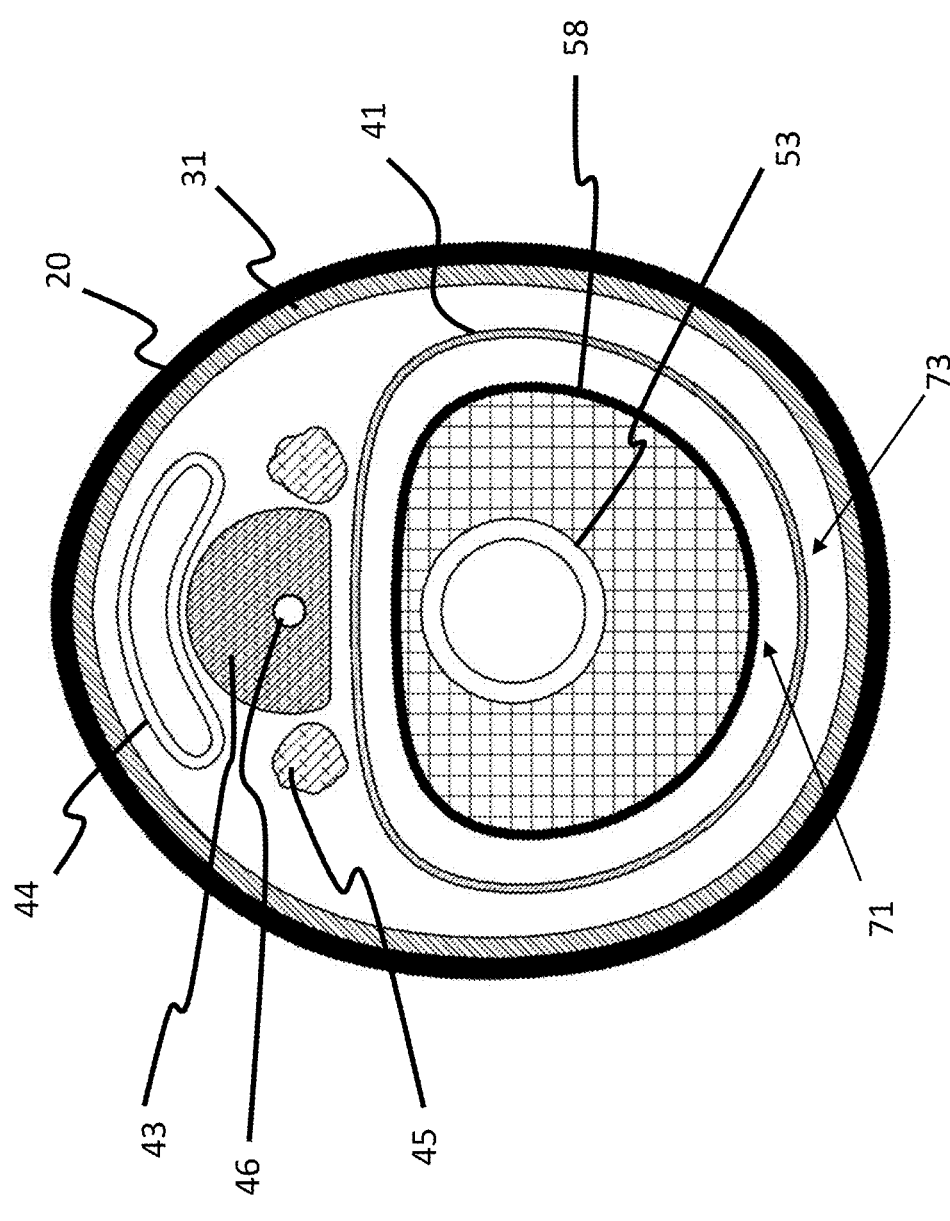

In reference to FIGS. 11A-11B, a before stretching/tension configuration is depicted in FIG. 11A and an after configuration is depicted in FIG. 11B, to illustrate an exemplary configuration in which the simulated endopelvic fascia 41 is not or minimally stretched or otherwise tensioned and the simulated mesorectum 58 is stretched considerably or otherwise tensioned relative to the simulated endopelvic fascia 41 in accordance with various embodiments of the present invention. In such a configuration, dissection in the holy plane 71 is easier than in the wrong plane 73 as the simulated mesorectum 58 tends to separate from the simulated endopelvic layer 41, as the mesorectum tends to return to its pre-stretched or non-stretched form. Easier holy plane dissection is less challenging or less difficult for a training surgeon as they will more likely dissect in the "correct" holy plane instead of the wrong plane.

Figure 12A:
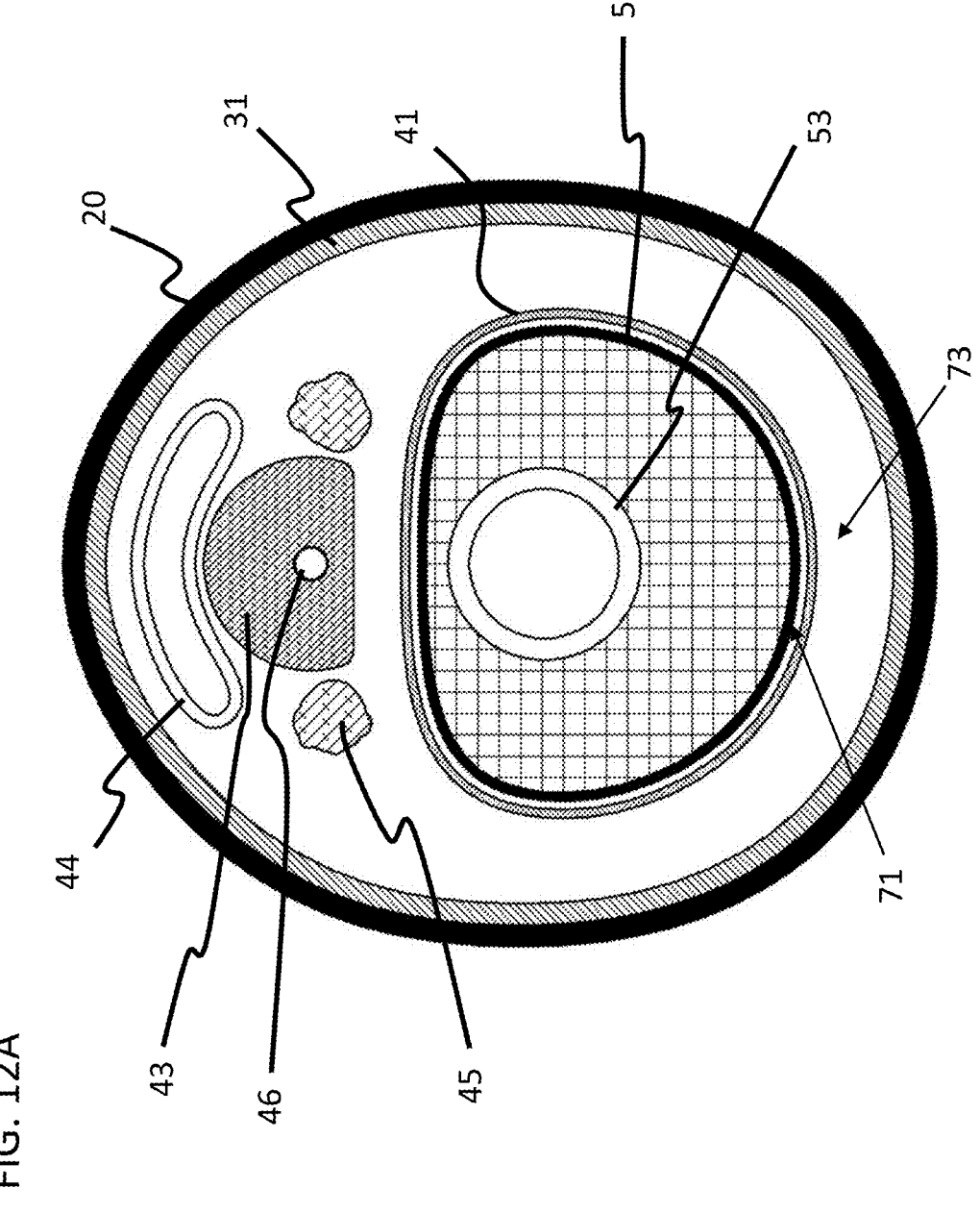
FIGS. 12A-12B are front cross-sectional semi-schematic diagrams of various configurations of a surgical simulator in accordance with various embodiments of the present invention.
Figure 12B:
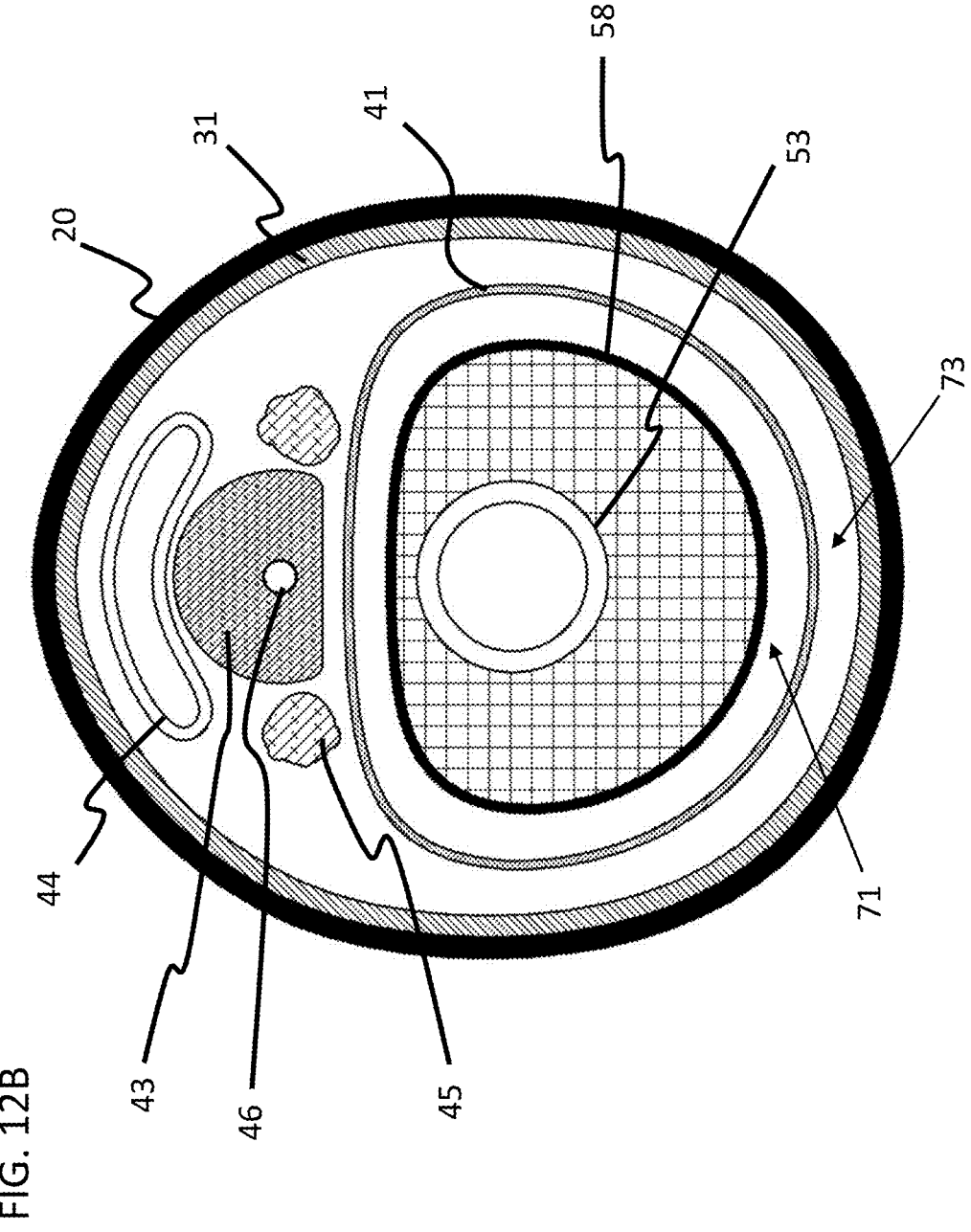

In reference to FIGS. 12A-12B, a before stretching/tension configuration is depicted in FIG. 12A and an after configuration is depicted in FIG. 12B, to illustrate an exemplary configuration in which the simulated mesorectum is not or minimally stretched or otherwise tensioned and the simulated endopelvic fascia 41 is stretched considerably or otherwise tensioned relative to the simulated mesorectum 58. In such a configuration, dissection in the wrong plane 73 is easier than in the holy plane 71 as the simulated mesorectum 58 would not tend to separate from the simulated endopelvic layer 41, the mesorectum having no or minimal tendency to bias to move inward or away from the endopelvic fascia layer 41. On the other hand, the simulated endopelvic layer would tend to separate from the simulated pelvic floor or towards the simulated mesorectum 58, as the simulated endopelvic layer 41 will tend to return to its pre-stretched or non-stretched form. Easier wrong plane dissection is more challenging or more difficult for a training surgeon as they may dissect in the wrong plane instead of the "correct" holy plane.

Figure 13:
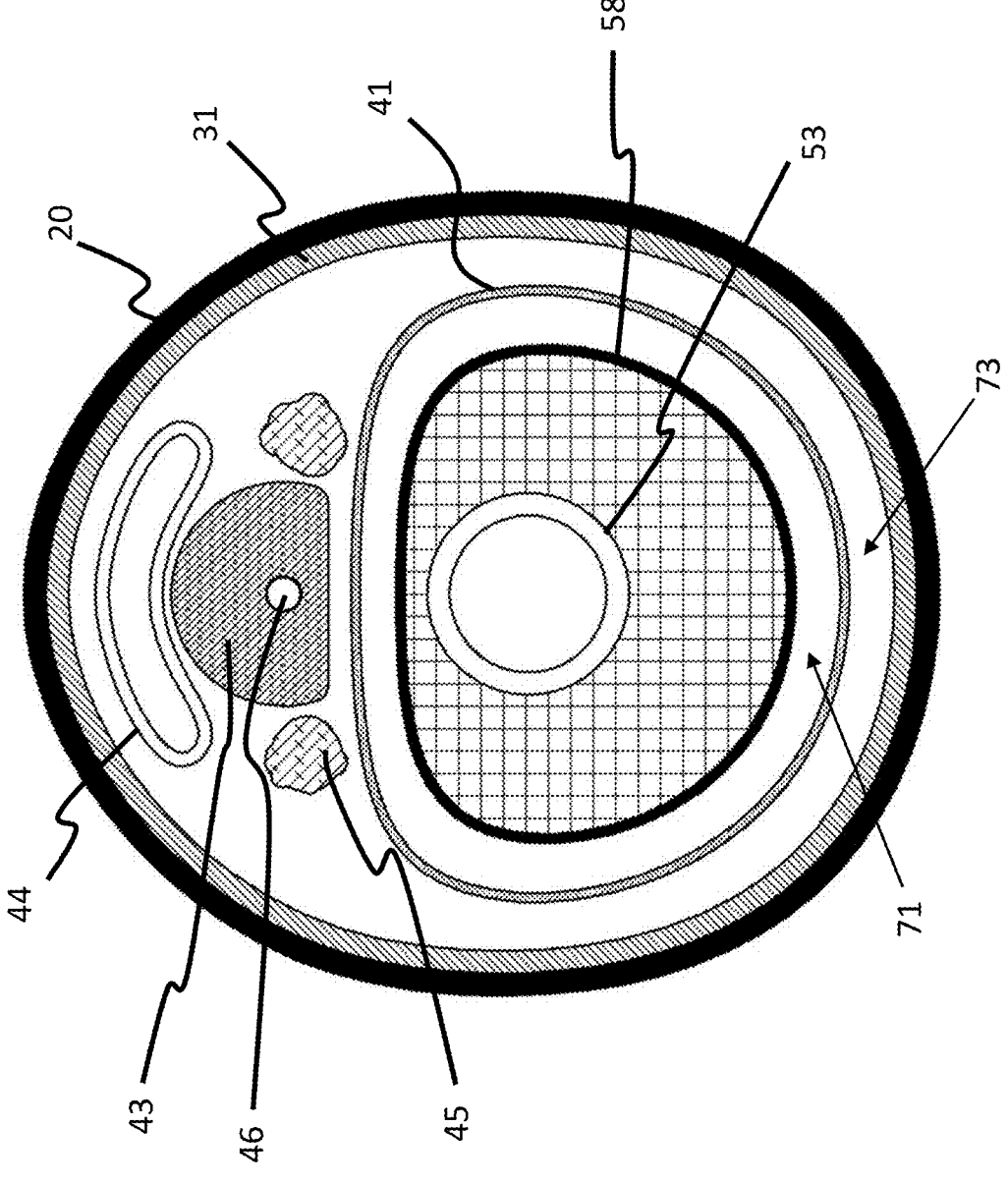
FIG. 13 is a front cross-sectional semi-schematic diagram of a configuration of a surgical simulator in accordance with various embodiments of the present invention.
Figure 14:
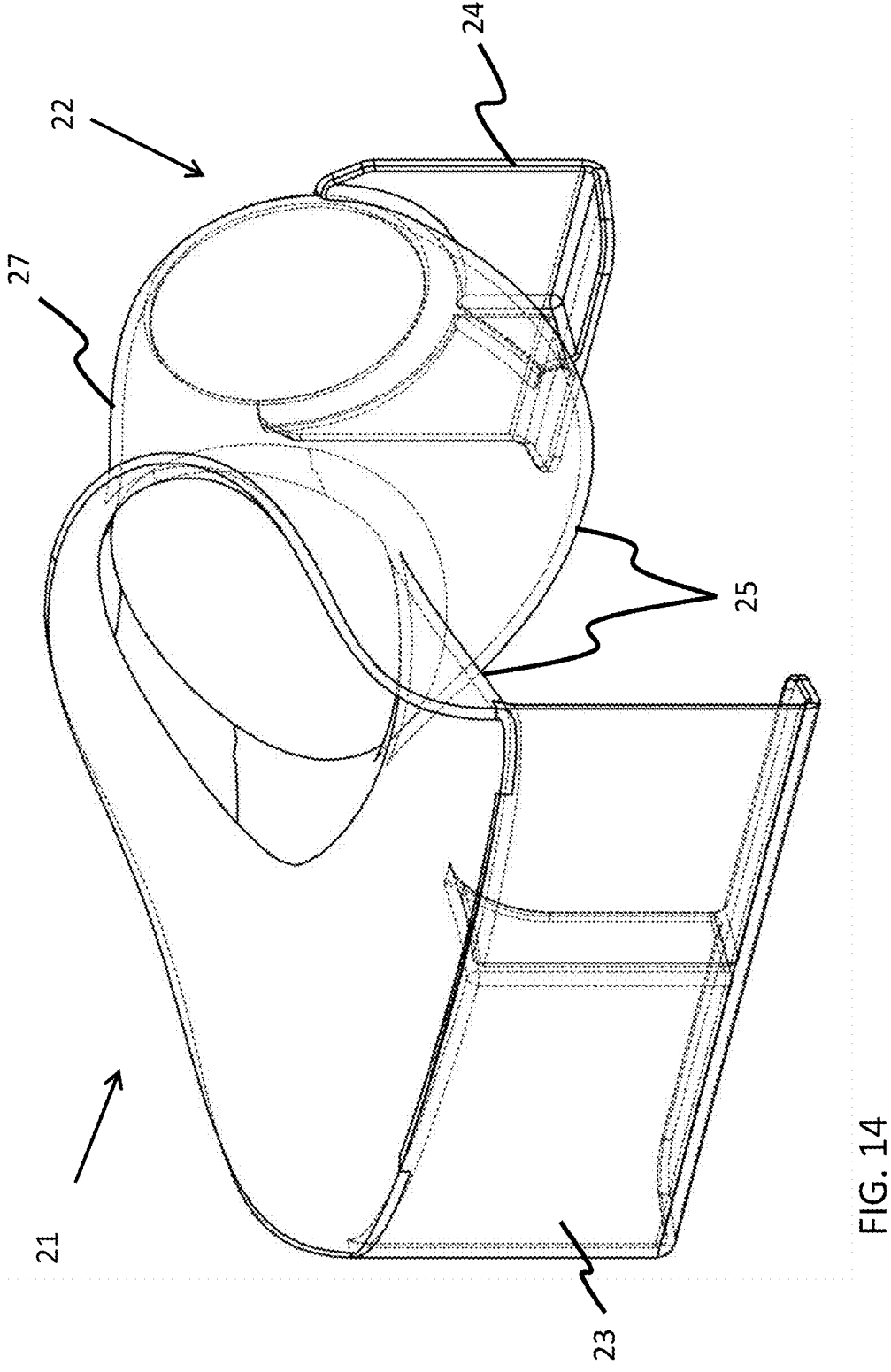
FIG. 14 is a perspective view of a frame of a surgical simulator in accordance with various embodiments of the present invention.
Figure 15:
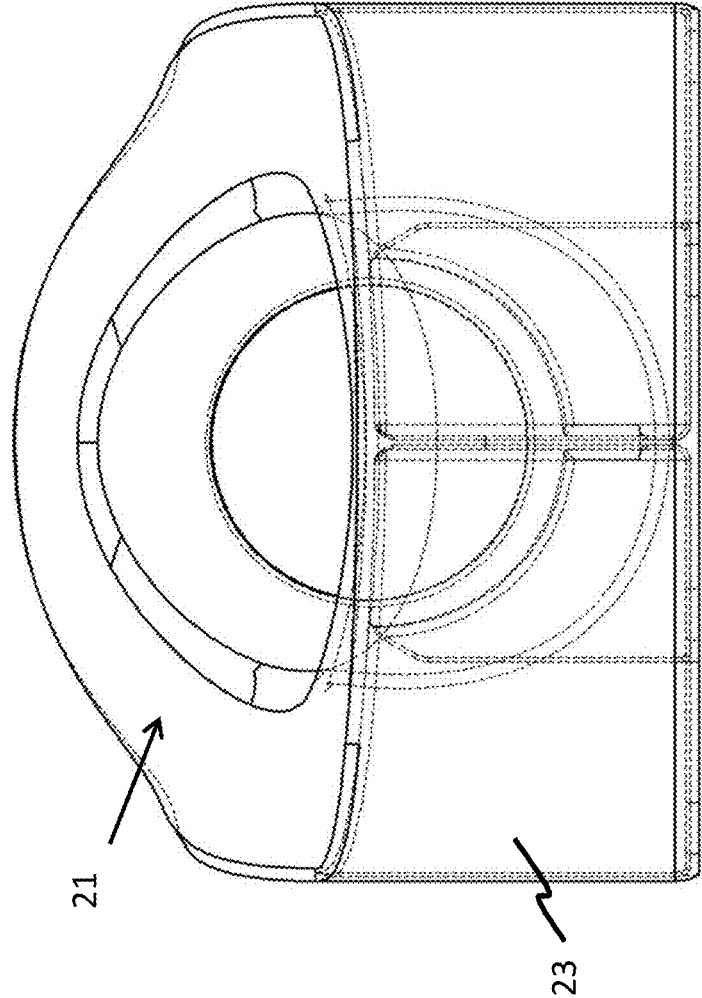
FIG. 15 is a front view of a frame of a surgical simulator in accordance with various embodiments of the present invention.
Figure 16:
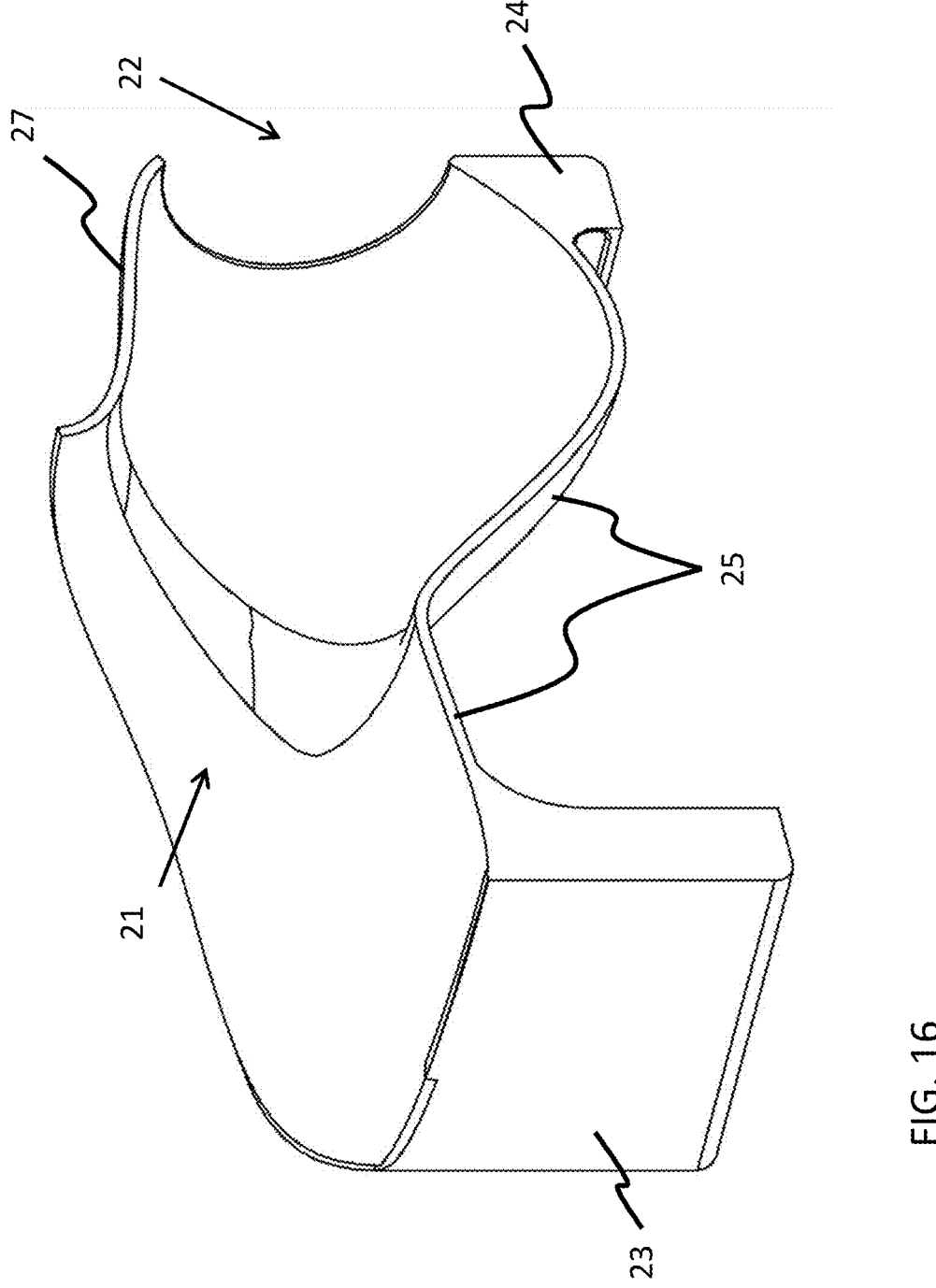
FIG. 16 is a perspective cross-sectional view of a frame of a surgical simulator in accordance with various embodiments of the present invention.
Figure 17:
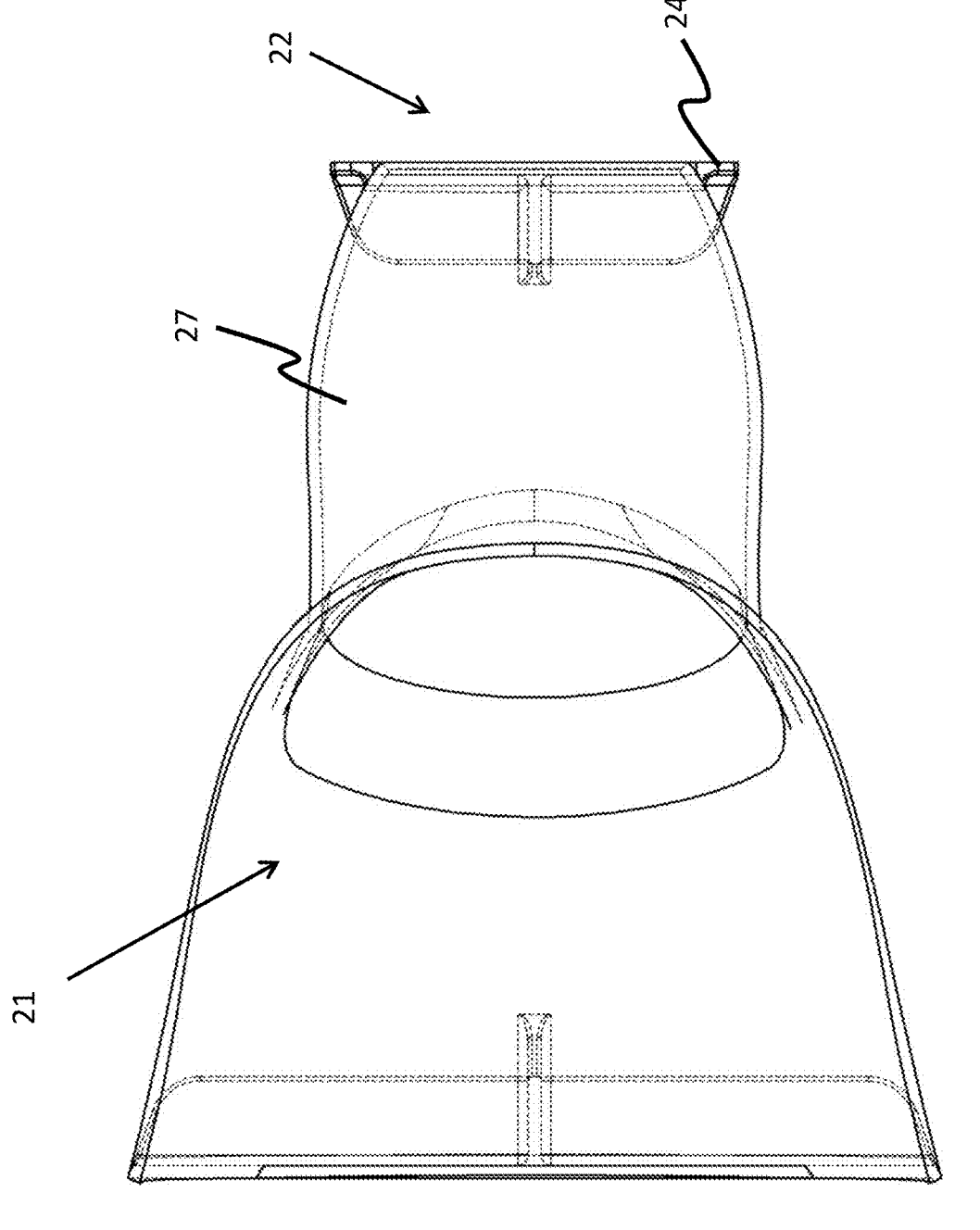
FIG. 17 is a top view of a frame of a surgical simulator in accordance with various embodiments of the present invention.

In reference to FIG. 13, a neutral or no/minimal stretching/tension configuration is depicted to illustrate an exemplary configuration in which the size of the simulated mesorectum and endopelvic fascia layers 58, 41 match the size of the frame and layer thickness of previous simulated layers so that they are adhered or otherwise attached in place without being placed under outward tension, stretching or the like. In this situation, in accordance with various embodiments, the difficulty of dissection is controlled or adjusted only by the fibrous material, pressure, adhesive/attachments and/or combinations thereof, as the layers are not subjected to outward tension and thus would not tend or be pre-conditioned to separate from each other. In various embodiments, as shown, for example, in FIG. 8B, the simulated endopelvic fascia and mesorectum layers 41, 58 are stretched or otherwise tensioned so that there is a simulated insufflation effect within both the holy and wrong planes 71, 73. In various embodiments, as such, the simulated endopelvic fascia layer 41 is stretched or otherwise tensioned more than the simulated mesorectum 58 so that the wrong plane dissection is slightly easier, but the simulated mesorectum is still stretched as well.

In various embodiments, the mesorectum fatty fill 61, e.g., a pre-made non-liquid fatty fill, is injected or otherwise introduced into the mesorectum/mesentery as one of the final steps. As a result, the fatty fill does not negatively affect the process of adhering or otherwise attaching the simulated tissue layers together and, in particular, the attachment between the mesorectum and endopelvic fascia can be enhanced to accurately simulate the holy plane of dissection between these two layers. Furthermore, in various embodiments, the outer layer of the mesorectum can be made very thin and fragile, e.g., made of a thin and fragile sheet of silicone, which enhances the realism of the TME surgical simulator and its ability to be used for assessment purposes.

In various embodiments, the simulated fatty fill comprises sodium polyacrylate, opaque agar gel, water and/or any combination thereof. It should be noted that gelatin and agar gels can be used for mesorectum fatty fill. However, gelatin melts at a low temperature (e.g., about 35°) thereby limiting its usefulness and agar gel exhibits syneresis when the gel is broken, which causes an unrealistic leaking of water from the mesorectum when the mesorectum is damaged.

It should be noted that various drawings are provided in a semi-schematic fashion to ease identifying and description of the TME surgical simulator. As such, the TME surgical simulator provided herein may intentionally not be made so uniform in places and/or the spacing between simulated structures as the drawings may suggest.

In various embodiments, a surgical simulator comprises a simulated parietal peritoneum layer, a simulated mesorectum and mesentery layer connected to the simulated parietal peritoneum layer and together forming a envelope there between. In various embodiments, the surgical simulator further comprises a simulated fatty fill disposed within the envelope. In various embodiments, the simulated fatty fill comprises sodium polyacrylate, agar gel, and/or a gel. In various embodiments, the simulated mesorectum and mesentery layer is puncturable and/or made of a thin puncturable silicone sheet.

In various embodiments, a surgical simulator comprises a frame having a proximal portion defining a simulated abdominal cavity and a distal portion defining a simulated pelvic cavity. In various embodiments, a simulated endopelvic fascia layer is disposed within the simulated pelvic cavity, a simulated pelvic floor layer is attached to the simulated endopelvic fascia layer and the distal portion of the frame. In various embodiments, a simulated mesorectum layer is attached to the simulated endopelvic fascia layer. In various embodiments, the simulated mesorectum layer and the simulated endopelvic fascia layer define a simulated dissection plane therebetween.

In various embodiments, the simulated endopelvic fascia layer, the simulated pelvic floor layer, the simulated mesorectum layer and/or any combination thereof are placed under circumferential tension, stretched, pre-stretched and/ or pre-tensioned. In various embodiments, the simulated endopelvic fascia layer is larger than the simulated pelvic floor layer. In various embodiments, the simulated endopelvic fascia layer is thicker and/or longer than the simulated pelvic floor layer.

In various embodiments, a surgical simulator comprises a frame having a proximal portion defining a simulated abdominal cavity and a distal portion defining a simulated pelvic cavity. In various embodiments, a simulated visceral peritoneum layer is disposed within the simulated abdominal cavity. In various embodiments, a simulated parietal peritoneum attached to the simulated visceral peritoneum layer and the proximal portion of the frame. In various embodiments, a simulated mesentery layer is attached to the simulated visceral peritoneum layer. In various embodiments, the simulated mesentery layer and the simulated visceral peritoneum layer define a simulated dissection plane therebetween.

In various embodiments, a surgical simulator comprises a simulated endopelvic fascia layer and a simulated mesorectum layer with at least one of the simulated endopelvic fascia layer and a simulated mesorectum layer are placed under circumferential tension, stretched, pre-stretched and/or pre-tensioned. In various embodiments, a surgical simulator comprises a simulated mesorectum layer and a simulated parietal peritoneum layer connected to each other and forming there between an envelope and a simulated fatty fill is disposed within the envelope. In various embodiments, a surgical simulator comprises a simulated endopelvic fascia layer and a simulated mesorectum layer, the simulated endopelvic fascia layer is attached to the simulated mesorectum layer to define a simulated dissection plane there between. In various embodiments, a surgical simulator comprises a simulated visceral peritoneum layer and a simulated mesentery layer, the simulated visceral peritoneum layer is attached to the simulated mesentery layer to define a simulated dissection plane there between. In various embodiments, a surgical simulator comprises a simulated pelvic floor layer and a simulated mesorectum layer, the simulated pelvic floor layer is attached to the simulated mesorectum layer to define a simulated dissection plane there between. In various embodiments, a surgical simulator comprises a simulated pelvic layer and a simulated mesentery layer, the simulated pelvic floor layer is attached to the simulated mesentery layer to define a simulated dissection plane there between. In various embodiments, a surgical simulator comprises a first composite silicone sheet connected to a second composite silicone sheet. In various embodiments, at least one of the first or second composite silicone sheets are placed under circumferential tension, stretched, pre-stretched and/or pre-tensioned. In various embodiments, a surgical simulator comprises a silicone sheet connected to a composite silicone sheet to define a simulated dissection plane there between. In various embodiments, a surgical simulator comprises a first composite silicone sheet connected to a second composite silicone sheet to define a simulated dissection plane there between. In various embodiments, a surgical simulator comprises a silicone sheet connected to a composite silicone sheet to form an envelope therebetween and a simulated fatty fill is disposed within the envelope. In various embodiments, a surgical simulator comprising a silicone envelope and a gel comprising at least one of sodium polyacrylate and opaque agar. In various embodiments, the simulated fascia layer is the simulated endopelvic fascia layer, the simulated Toldt's fascia/visceral peritoneum layer, the simulated Toldt's fascia, the Toldt's/endopelvic fascia layer and/or any combination thereof. In various embodiments, the surgical simulator does not include a frame or base and/or in various embodiments includes one or more simulated structures, components and the like without a frame or the like.

The above description is provided to enable any person skilled in the art to make and use the present invention and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A surgical simulator for a simulated surgical procedure, the surgical simulator comprising:

a frame having a cavity, a proximal opening, and a distal opening;

a plurality of simulated tissue layers disposed within the frame and attached, at least partially, to each other, wherein two or more of the plurality of simulated tissue layers are configured to define at least one dissection plane whereby the two or more of the plurality of simulated tissue layers are configured to be separable from each other, wherein one or more of the plurality of simulated tissue layers are configured with an outward tension away from an interior of the cavity of the frame to simulate insufflation, with a first simulated tissue layer of the one or more plurality of simulated tissue layers and a second simulated tissue layer of the one or more plurality of simulated tissues layers having differing outward tensions away from the interior of the cavity of the frame;

wherein the plurality of simulated tissue layers comprise a simulated endopelvic fascia layer, a simulated mesorectum layer, and a simulated pelvic floor having an upper portion covering an upper portion of the frame and a lower portion attached to and covering a lower portion of the frame, the lower portion of the simulated pelvic floor extending from the proximal opening of the frame and extending beyond the distal opening of the frame; and wherein the simulated surgical procedure corresponds to a simulated total mesorectal excision (TME procedure.

2. The surgical simulator of claim 1, wherein a first set of adjacent simulated tissue layers of the plurality of simulated tissue layers in the at least one dissection plane have a first tactile response when being separated and due to at least one simulated tissue layer of the first set of adjacent simulated tissue layers having an outward tension away from the interior of the cavity of the frame, the first tactile response is different from a second tactile response of a second set of adjacent simulated tissue layers of the plurality of simulated tissue layers not in the at least one dissection plane when being separated.

3. The surgical simulator of claim 2, wherein the first tactile response corresponds to separation of the first set of adjacent simulated tissue layers in the at least one dissection plane being easier due to at least one simulated tissue layer of the first set of adjacent simulated tissue layers having an outward tension away from the interior of the cavity of the frame compared to separation of the second set of adjacent simulated tissue layers of the plurality of simulated tissue layers not in the at least one dissection plane.

4. The surgical simulator of claim 3, wherein the second set of adjacent simulated tissue layers of the plurality of simulated tissue layers not in the at least one dissection plane are attached to each other via adhesive to provide the second tactile response.

5. The surgical simulator of claim 2 wherein two or more layers of the plurality of simulated tissue layers further comprises fibrous material, wherein the fibrous material is configured to provide a third tactile response during separation of the two or more layers of the plurality of simulated tissue layers comprising the fibrous material, the third tactile response being different from the first tactile response and the second tactile response.

6. The surgical simulator of claim 1 further comprising fatty fill enclosed within the plurality of simulated tissue layers.

7. The surgical simulator of claim 1, wherein one or more simulated tissue layers of the plurality of simulated tissue layers comprise conductive material configured for electrosurgical energy-based dissection.

8. The surgical simulator of claim 1 wherein the plurality of simulated tissue layers are configured to have portions with different textures from one another, a first portion having a first texture corresponding to the at least one dissection plane and a second portion having a second texture that is not within the at least one dissection plane.

9. The surgical simulator of claim 1, wherein the first simulated tissue layer is stretched and has an outward tension away from the interior of the cavity of the frame greater than an outward tension of the second simulated tissue layer away from the interior of the cavity of the frame, increasing difficulty of dissection in a dissection plane between the first simulated tissue layer and the second simulated tissue layer.

10. The surgical simulator of claim 1, wherein the first simulated tissue layer is stretched and has an outward tension away from the interior of the cavity of the frame and the second simulated tissue layer less than an outward tension of the second simulated tissue layer away from the interior of the cavity of the frame, decreasing difficulty of dissection in a dissection plane between the first simulated tissue layer and the second simulated tissue layer.

11. A surgical simulator for a simulated surgical procedure, the surgical simulator comprising:
  a frame having a proximal end and a distal end;
  a plurality of simulated tissue layers disposed within the frame and attached, at least partially, to each other, wherein two or more of the plurality of simulated tissue layers are configured to define at least one dissection plane whereby the two or more of the plurality of simulated tissue layers are configured to be separable from each other, and wherein one or more of the plurality of simulated tissue layers are configured with an outward tension to simulate insufflation; and
  a balloon comprises silicone and fibrous material composite and contains a fatty fill, the balloon being attached circumferentially to other silicone-based simulated tissue layers of the plurality of simulated tissue layers and extending from the proximal end of the frame to the distal end of the frame, wherein the balloon has a proximal portion at the proximal end of the frame and a distal portion at the distal end of the frame, the distal portion of the balloon being larger than the proximal portion of the balloon.

12. The surgical simulator of claim 11, wherein the fatty fill is configured to leak or escape when a portion of the balloon is punctured.

13. The surgical simulator of claim 12, wherein the fatty fill is gel like, and wherein the fatty fill is configured to retain its shape within the balloon simulating a mesorectum even if the balloon is punctured.

14. The surgical simulator of claim 13, wherein the balloon is configured to be removed from the plurality of simulated tissue layers, wherein the balloon is configured to comprise at least one of visual voids or lumps indicative of where the fatty fill leaked or escaped and configured to be graded thereby quantifying a performance of the simulated surgical procedure.

15. The surgical simulator of claim 12, wherein the fatty fill further comprises fibrous material configured to prevent unrealistic ejection of the fatty fill when the balloon is punctured.

16. The surgical simulator of claim 11 further comprising one or more simulated organs including a simulated rectum, simulated ureter, a simulated colon, a simulated prostrate, and simulated Gonadal vessels, the simulated rectum being tubular and extending into and through the distal portion of the balloon, in which a portion of the simulated rectum is configured to be removed along with the balloon attached thereto.

17. A surgical simulator for a simulated surgical procedure, the surgical simulator comprising:
  a frame having a proximal end and a distal end;
  a first simulated tissue layer disposed within the frame;
  a second simulated tissue layer disposed within the frame and attached the first simulated tissue layer, the first and second simulated tissue layers being configured to define a dissection plane in which the first and second simulated tissue layers are configured to be separable from each other, at least one of the first and second simulated tissue layers being placed under circumferential tension; and
  a third simulated tissue layer attached to the first simulated tissue layer and to the distal end of the frame, the third simulated tissue layer being stretched towards an interior of the frame and attached to a simulated vessel and a simulated organ, wherein the third simulated tissue layer has an upper portion attached to and covering an upper portion of the frame and a lower portion attached to and covering a lower portion of the frame, the lower portion of the third simulated tissue layer extending from a proximal opening at the proximal end of the frame and extending beyond a distal opening at the distal end of the frame;
  wherein the first and second simulated tissue layers are both placed under circumferential tension and the first simulated tissue layer is circumferentially tensioned more than the second simulated tissue layer.

* * * * *